United States Patent
Feghali et al.

(10) Patent No.: US 10,081,644 B2
(45) Date of Patent: Sep. 25, 2018

(54) METHOD OF PREPARING AROMATIC COMPOUNDS FROM LIGNIN

(71) Applicant: Commissariat A L'energie Atomique Et Aux Energies Alternatives, Paris (FR)

(72) Inventors: Elias Feghali, Montrouge (FR); Thibault Cantat, Issy les Moulineaux (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/323,547

(22) PCT Filed: Jun. 17, 2015

(86) PCT No.: PCT/IB2015/054570
§ 371 (c)(1),
(2) Date: Jan. 3, 2017

(87) PCT Pub. No.: WO2016/005837
PCT Pub. Date: Jan. 14, 2016

(65) Prior Publication Data
US 2017/0137446 A1    May 18, 2017

(30) Foreign Application Priority Data
Jul. 9, 2014    (FR) ...................................... 14 56638

(51) Int. Cl.
*C07F 7/04*    (2006.01)
*C07F 7/18*    (2006.01)

(52) U.S. Cl.
CPC .................................. *C07F 7/1852* (2013.01)

(58) Field of Classification Search
CPC .................................................... C07F 7/1852
USPC ......................................................... 556/432
See application file for complete search history.

(56) References Cited

FOREIGN PATENT DOCUMENTS

| WO | WO 2011/003029 A2 | 1/2011 | |
| WO | WO 2011003029 A2 * | 1/2011 | .......... B01J 31/2243 |

OTHER PUBLICATIONS

Zhang et al., ACS Sustainable Chem. Eng. 2014, 2, 1983-1991.*
Zhang et al., (ACS Sustainable Chem. Eng. 2014, 2, 1983-1991).*
International Search Report and Written Opinion from corresponding International Patent Application No. PCT/IB2015/054570 dated Sep. 24, 2015.
Jianfeng Zhang et al.; "Reductive Degradation of Lignin and Model Compounds by Hydrosilanes"; ACS Sustainable Chemistry & Engineering; vol. 2, No. 8; Jul. 3, 2014; pp. 1983-1991; XP055171789.
Elias Feghali et al.; "Unprecedented Organocatalytic Reduction of Lignin Model Compounds to Phenols and Primary Alcohols Using Hydrosilanes"; Chemical Communications; vol. 50, No. 7; Jan. 1, 2014; pp. 862-865; XP055171824.

* cited by examiner

*Primary Examiner* — Clinton Brooks
*Assistant Examiner* — Kofi Adzamli
(74) *Attorney, Agent, or Firm* — Alston & Bird LLP

(57) ABSTRACT

The invention relates to a method of preparing monocyclic aromatic compounds from lignin and to the use of the method and/or the aromatic compounds obtained by the method according to the invention in the production of fuels, electronic components, plastic polymers, rubber, medicines, vitamins, cosmetic products, perfumes, foodstuffs, synthetic threads and fibers, synthetic leathers, adhesives, pesticides and fertilizers. The invention also relates to a method of producing fuels, electronic components, plastic polymers, rubber, medicines, vitamins, cosmetic products, perfumes, foodstuffs, synthetic threads and fibers, synthetic leathers, adhesives, pesticides and fertilizers, including a step of preparing aromatic compounds from lignin using the method according to the invention.

18 Claims, 7 Drawing Sheets

| Bond | Softwood (spruce) % | Hardwood (birch) % |
| --- | --- | --- |
| β-O-4 | 46 | 60 |
| α-O-4 | 6-8 | 6-8 |
| 4-O-5 | 3.5-4 | 6.5 |
| β-5 | 9-12 | 6 |
| 5-5 | 9.5-11 | 4.5 |
| β-1 | 7 | 7 |
| β-β | 2 | 3 |
| Others | 13 | 5 |

FIGURE 3

1-silacyclo-3-pentene 1-methyl-1-hydrido-2,3,4,5-tetraphenyl-1-silacyclopentadiene

METHOD OF PREPARING AROMATIC COMPOUNDS FROM LIGNIN

FIELD

The present invention relates to a process for preparing monocyclic aromatic compounds from lignin and to the use of said process and/or of said aromatic compounds obtained by means of the process of the invention in the production of fuels, electronic components, plastic polymers, rubber, medicaments, vitamins, cosmetic products, fragrances, foodstuffs, synthetic threads and fibers, synthetic leathers, adhesives, pesticides and fertilizers.

It also relates to a process for producing fuels, electronic components, plastic polymers, rubber, medicaments, vitamins, cosmetic products, fragrances, foodstuffs, synthetic threads and fibers, synthetic leathers, adhesives, pesticides and fertilizers, comprising a step of preparing aromatic compounds from lignin by means of the process according to the invention.

BACKGROUND

Wood is composed of three major constituents: cellulose, hemicellulose and lignin. Cellulose and hemicellulose are already exploited industrially, in particular in the paper industry. This use generates each year several million metric tons of lignin-rich by-products which are used as fuels of low heat-generating capacity for supplying heat and energy to paper production processes. In parallel, a minimum amount of lignin is isolated by direct extraction from plants (F. G. Calvo-Flores and J. A. Dobado, *ChemSusChem.* 2010, 3, pages 1227-1235).

Lignin is the most abundant substance, in terms of source, of aromatic groups in nature and the biggest contributor to the soil of organic matter (S. Y. Lin, in Methods in Lignin Chemistry, Springer Series in Wood Science (Ed.: C. W. Dence), Springer, Berlin 1992). It essentially results from the radical polymerization of three monomers called monolignols: p-coumarilyl alcohol, coniferyl alcohol and sinapyl alcohol, which, after polymerization by dehydrogenation with peroxidase, give respectively the p-hydroxyphenyl (H), guaiacyl (G) and syringyl (S) residues, as illustrated in FIG. 1 (R. Vanholme, K. Morreel, J. R. W. Boerjan, *Curr. Opin. Plant Biol.* 2008, 11, pages 278-285).

The complexity and also the diversity of the structure of lignin is dependent to a large extent on its origin. Using plant taxonomy as a basis, it has been proposed that the lignin derived from gymnosperms (called softwood) has more G residues than that derived from angiosperms (called hardwood), which contain a mixture of G and S residues, and the lignin derived from herbaceous plants contains a mixture of the three aromatic residues H, G and S. A more rigorous classification technique has been to use, as a basis, a chemical approach in which the lignins are classified according to abundance of the G, H and S units in the polymer. Four major lignin groups have thus been identified: G-type, GS-type, HGS-type and HG-type (F. G. Calvo-Flores and J. A. Dobado, *ChemSusChem.* 2010, 3, pages 1227-1235).

Whatever the lignin type, this biopolymer is characterized by a great biochemical heterogeneity and consists of propylphenol units bonded to one another by means of various types of C—O and C—C bonds of aryl ether, aryl glycerol and β-aryl ether type. FIG. 2 shows the structure of lignin proposed by E. Adler, *Wood Sci. Technol.* 1977, 11, page 169.

Ether bonds represent approximately two thirds of the bonds. More specifically, bonds of β-O-4 and α-O-4 type, which are among the alkylaryl ethers, are the most abundant. Typically, the lignin of angiosperms (hardwood) contains 60% of bonds of β-O-4 type and 6-8% of α-O-4 type, and the lignin derived from gymnosperms (softwood) contains 46% of bonds of β-O-4 type and 6-8% of α-O-4 type. Although the proportion of these bonds varies considerably from one species to another, typical values taken from M. P. Pandey, C. S. Kim, *Chem. Eng. Technol.*, 2011, 34, 29, have been listed in the table of FIG. 3.

The chemical structures of the most abundant types of bond present in lignin are represented in FIG. 4.

Lignin represents the greatest renewable reservoir of available aromatic compounds. Because of its high content of aromatic compounds, lignin has a high potential to operate as an alternative to non-renewable fossil resources for the production of aromatic chemical products with a high added value, that is to say products of which the conversion considerably increases their commercial value. By way of aromatic chemical products with a high added value, mention may be made, for example, of 4-hydroxy-3-methoxybenzaldehyde or vanillin, 4-propylbenzene-1,2-diol or 4-(3-hydroxypropyl)-1,2-benzenediol.

Thus, the exploitation of lignin involves its conversion into precious and useful aromatic products. At the current time, few products, in particular aromatic products, that are pure or that can be easily purified, are obtained directly from lignin giving the very heterogeneous structure of lignin comprising several types of residues and of different bonds, the great difficulty in performing a selective cleavage of the lignin bonds, and also the difficulty in purifying the final mixtures obtained. Indeed, at the current time, the processes for producing aromatic products from lignin generate a large number of products which have physical and chemical properties that are similar to one another. Thus, separating them, in particular into a pure product, is very difficult using conventional purification techniques (chromatography or distillation). The only and most significant aromatic product obtained from lignin is 4-hydroxy-3-methoxybenzaldehyde or vanillin.

M. B. Hocking, *J. Chem. Educ.*, 1997, 74, pages 1055-1059, has described the synthesis of vanillin from lignin sulfonates (lignin resulting from the sulfite process). However, this process has some drawbacks, in particular the production of large amounts of waste effluents (160 kg of caustic liquids for each kg of vanillin produced). Given the increasing awareness of the public regarding environmental issues, the costs of treating the non-sustainable effluents have become high and, consequently, factories using this vanillin synthesis process have begun to close.

Since 1993, the Norwegian company Borreegaard has constituted the only producer of vanillin from lignosulfonate. The key step of this process, initially developed by Monsanto, is the oxidation reaction which is carried out using a copper-based catalyst, said catalyst being subsequently recycled. This step is illustrated in FIG. 5.

This process uses an ultrafiltration technique coupled to a reverse osmosis technique, which makes it possible to reduce the volume of the waste streams and also to increase the vanillin yield (U.S. Pat. No. 4,151,207). This process makes it possible to obtain, from 1000 kg of wood: 400 kg (40%) of specialty cellulose, 400 kg (40%) of lignin, 3 kg (0.3%) of vanillin, 20 kg (2%) of yeast, 50 kg (5%) of ethanol and 45 kg (4.5%) of $CO_2$, with exploitation of the heat generated by the process as described by F. G. Calvo-Flores and J. A. Dobado, *ChemSusChem.*, 2010, 3, pages 1227-1235. The vanillin yield by means of this process is very low with respect to vanillin (less than 1%). Moreover, this process allows the synthesis of vanillin alone given that it is based essentially on the presence of G residues. The aromatic molecules derived from the other residues have not been exploited by means of this process.

The exploitation of lignin involving its conversion into precious and useful aromatic products continues to create a great deal of interest. The major problem for chemists is to develop, from lignin, processes:

which can deal with the variable characteristics of the structure of lignin, and which make it possible to produce aromatic chemical compounds conventionally obtained by petrochemical methods, with good purity or which can be easily purified, and which will be able to serve as basic compounds in the production of fuels, electronic components, plastic polymers, rubber, medicaments, vitamins, cosmetic products, fragrances, foodstuffs, synthetic threads and fibers, synthetic leathers, adhesives, pesticides, fertilizers, etc.

There is thus a real need for a process which allows the preparation of an aromatic compound, of good purity (at least 90% by weight, relative to the total weight of the aromatic compounds obtained) or which can be easily purified, from lignin, and which overcomes the drawbacks of the prior art.

In particular, there is a real need for a process which allows the preparation of an aromatic compound from lignin, said process:

making it possible to prepare aromatic compounds, in particular monocyclic aromatic compounds, with good purity (at least 90% by weight, relative to the total weight of the aromatic compounds obtained) or which can be easily purified;

having a selectivity which can be adjusted according to the aromatic compounds that it is sought to prepare;

being able to adapt to the versatility and heterogeneity of lignin, which depend on the type of vegetation from which the lignin originates and also on the process for the extraction thereof;

having a high productivity which results in a high conversion of lignin into aromatic compounds of good purity or which can be easily purified;

being able to be carried out under mild and industrially advantageous operating conditions; and/or being simple to carry out.

The development of a convergent depolymerization process may thus significantly contribute to the exploitation of lignin through its conversion into useful aromatic products while at the same time meeting the abovementioned requirements. The principle of a convergent lignin depolymerization process is to result in the reduction of the lignin into small oligomers which differ in terms of their degree of oxygenation. The latter are reduced (deoxygenated) gradually so as to converge toward a single product which accumulates in the reaction medium. However, lignin depolymerization is difficult and represents a challenge, since its structure is highly functionalized and branched and its steric hindrance can limit the access of the catalyst to the active sites. Furthermore, the chemical heterogeneity of lignin, which is due to the presence of several G, H and S residues present in variable amounts depending on the plant source, and to the presence of various types of C—O and C—C bonds of aryl ether, aryl glycerol and β-aryl ether type, complicates the obtaining of pure chemical products during the conversion of lignin.

Given the difficulty in performing a direct depolymerization of lignin, scientists have synthesized chemically pure models, representative of the ether bonds present in the lignin, in order to study the reactivity thereof (J. Zakzeski, P. C. A. Bruijnincx, A. L. Jongerius and B. M. Weckhuysen, *Chem Rev.*, 2010, 110, page 3552). The majority of the studies targeting lignin depolymerization have focused on these models and have not been able to be carried out on the complex structure of natural lignins. Various organometallic complexes have been used to catalyze the reactions carried out on the models of ether bonds in lignin, for instance:

ruthenium (a) J. M. Nichols, L. M. Bishop, R. G. Bergman, J. A. Ellman, *J. Am. Chem. Soc.* 2010, 132, pages 12554-12555; b) A. Wu, B. O. Patrick, E. Chung and B. R. James, *Dalton Trans.*, 2012, 41, page 11093; c) T. vom Stein, T. Weigand, C. Merkens, Jurgen Klankermayer, W. Leitner, *ChemCatChem*, 2013, 5, pages 439-441), vanadium (S. Son and F. D. Toste, *Angew. Chem. Int. Ed.* 2010, 49, pages 3791-3794), and nickel (AG. Sergeev and J. F. Hartwig, *Science,* 2011, 332, page 439).

Given the complex, heterogeneous and highly hindered polymeric structure of lignin which complicates its depolymerization, the depolymerization processes developed in the literature are generally carried out under drastic temperature and pressure conditions and use metals in high catalytic amounts. Furthermore, processes that it has been possible to extrapolate from the chemically pure models to the depolymerization of lignin are rare. In 2013, the first organocatalytic reduction of model compounds of lignin was described by Feghali and Cantat (E. Feghali, T. Cantat, *Chem. Commun.,* 2014, 50, pages 862-865). The latter showed that $B(C_6F_5)_3$ is an efficient and selective hydrosilylation catalyst for the reductive cleavage of alkylaryl ether bonds and, in particular, of the models of α-O-4 and β-O-4 units. Furthermore, the reduction was carried out under mild conditions (ambient temperature for from 2 to 16 hours), and could be carried out with an inexpensive and air-stable hydride source such as polymethylhydrosiloxane (PMHS) or tetramethyldisilazane (TMDS). Nevertheless, this process could not be extrapolated to the depolymerization of lignin.

At the current time, there is no process for reductive depolymerization of lignin for preparing aromatic compounds. The only processes which describe the depolymerization of lignin in homogeneous catalysis are those carried out described by Toste et al. and Ragauskas et al.

It has been possible to extrapolate the process of Toste et al., which was developed on models of C—O bonds of the β-O-4 unit of lignin (S. Son and F. D. Toste, *Angew. Chem. Int. Ed.* 2010, 49, pages 3791-3794), to the lignin extracted from *Miscanthus giganteus* or elephant grass (J. M. W. Chan, S. Bauer, H. Sorek, S. Sreekumar, K. Wang, F. D. Toste, *ACS Catal.,* 2013, 3, pages 1369-1377). In this process, a vanadium catalyst was used by Toste et al. for the cleavage of C—O bonds of the β-O-4 unit of lignin and the formation of aryl enones. This redox conversion is carried out in ethyl acetate at 80° C. for 24 h. The catalyst load is 10% by weight. The results of the dioxasolv and acetosolv lignin depolymerization CPG and 2D NMR studies resembled the data obtained with the lignin models, thereby confirming the selectivity for β-O-4 bonds. Finally, the authors were able to identify and quantify, by GC/MS, volatile phenolic compounds (such as vanillin, vanillic acid, syringic acid and syringaldehyde) produced in the reaction. Nevertheless, no chemical product could be isolated pure from this process and partially characterized complex mixtures were obtained with low yields for each product. Indeed, in the case of Toste et al., the depolymerization is carried out on grasses which are already made up of a mixture of the three residues H, G and S, and the process carried out is a redox process which, instead of converging the products obtained toward a single product, keeps the same diversity of products obtained as that present in the starting lignin.

The groups of Toste, Ellman and Hartwig grouped together their results on lignin reduction and models for the homogeneous catalysis thereof in international application WO 2011/003029. The precursors used are vanadium derivatives, ruthenium derivatives and rhodium derivatives. Only the vanadium-based and ruthenium-based complexes were used for the redox depolymerization of lignin extracted from *Miscanthus giganteus*. Nevertheless, no pure chemical product could be isolated or identified by means of this process and partially characterized mixtures were obtained.

In 2009, Ragauskas et al. (M. Nagy, K. David, G. J. P. Britovsek and A. J. Ragauskas, *Holzforschung*, 2009, 63, page 513) succeeded in depolymerizing organosolv ethanol lignin (EOL) (soluble in ethanol) derived from pine under reducing conditions. In this study, conventional heterogeneous catalysts and also new homogeneous catalysts were used for the cleavage of diaryl ether and dialkyl ether bonds. When using the hydrogenolysis conditions: 5 MPa $H_2$; 175° C.; 20 hours, the ruthenium catalyst effectively increases lignin solubility (solubility up to 96%) and contributes to the degradation thereof. A decrease of about 10% to 20% of the weight-average molar mass (Mw) was obtained (Mw=1900-2100 g/mol), which corresponds to a degree of polymerization (DP) of 10 to 11 monomer units (L. B. Davin, L. B., N. G. Lewis, *Curr. Opin. Biotechnol.*, 2005, 16, pages 407-415). Furthermore, according to the authors, the hydrogenolysis of the diaryl ether and alkylaryl ether groups is accompanied by a reaction of simultaneous hydrogenation of the aromatic ring and it is thus not possible to isolate aromatic compounds. Finally, the identification and also the detailed formation of the reaction products and of the cleavage pathways were not elucidated given that the products obtained are oligomers of which the structure is very difficult to identify. Ragauskas et al. neither mention nor obtain molecules of low molar masses.

As already indicated, because of its high content of aromatic compounds, lignin has a great potential for operating as an alternative to non-renewable fossil resources for the production of aromatic chemical products with a high added value. However, because of its amorphous structure, which is very diversified in terms of residues contained, which use polymeric based on strong ether bonds, which contains a large number of bonds of different types, its polymerization to selectively produce usable molecules represents a challenge (P. J. Deuss, K. Barta and J. G. de Vries, *Catal. Sci. Technol.*, 2014, Accepted Manuscript; DOI: 10.1039/C3CY01058A). In addition, lignins are structurally very diversified and, depending on the plant source used, they can contain different proportions of the three base monomers, namely p-coumaryl alcohol, coniferyl alcohol and sinapyl alcohol.

There is thus a real need for a process which allows the preparation of an aromatic compound from lignin and which can implement a lignin depolymerization step overcoming the drawbacks of the prior art.

SUMMARY

In particular, there is a real need for a process which allows the preparation of an aromatic compound from lignin, said process:

making it possible to prepare vanillin but also other aromatic compounds, in particular monocyclic aromatic compounds, with good purity (at least 90% by weight of the desired monocyclic aromatic compound, relative to the total weight of the monocyclic aromatic compounds obtained) or which can be easily purified;

having a high productivity which results in a high conversion of lignin to aromatic compounds of good purity or which can be easily purified;

having a selectivity that can be modulated with respect to the aromatic compound(s) that it is sought to prepare;

being able to be carried out under mild and industrially advantageous operating conditions;

carrying out a lignin depolymerization step:
  which is simple to carry out;
  which can be carried out under mild and industrially advantageous operating conditions;
  which can adapt to the versatility and to the heterogeneity of the lignin, which are characteristics that depend on the type of vegetation from which the lignin originates and on the process for the extraction thereof;
  which allows selective cleavage of certain lignin bonds.

The objective of the present invention is precisely to meet these needs by providing a process for preparing monocyclic aromatic compounds of formula (I)

in which
  $R^1$, $R^2$ and $R^3$, represent, independently of one another, a hydrogen atom, a hydroxyl group, an alkoxy group or a siloxy group;
  Y represents an alkyl group, an alkenyl group, an alkynyl group, or a carbonyl group —$CR^4$=O with $R^4$ representing a hydrogen atom, an alkyl group, a hydroxyl group or an alkoxy group;
  said alkyl, alkenyl and alkynyl groups being optionally substituted;

characterized in that it comprises a step of depolymerization of the lignin by selective cleavage of the carbon $sp^3$-oxygen bond of the alkylaryl ethers of the β-O-4, α-O-4, β-5, β-1 and β-β type present in the lignin, said depolymerization step comprising the reaction, of a lignin containing a sulfur content of less than 1.5% by weight, relative to the total weight of the lignin, with a silane compound of formula (II)

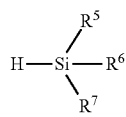
(III)

in which
R$^5$, R$^6$ and R$^7$ represent, independently of one another, a hydrogen atom, a halogen atom, a hydroxyl group, an alkyl group, an alkenyl group, an alkynyl group, an alkoxy group, an aryloxy group, a silylated group, a siloxy group, an aryl group or an amino group, said alkyl, alkenyl, alkynyl, alkoxy, silylated, siloxy, aryl and amino groups being optionally substituted, or R$^7$ is as defined above and R$^5$ and R$^6$, taken together with the silicon atom to which they are bonded, form an optionally substituted, silylated heterocycle;

in the presence of a catalyst.

BRIEF DESCRIPTION OF THE DRAWINGS

FIG. 3 provides a table showing typical proportions values of ether bonds in softwood (spruce) and hardwood (birch) trees;

DETAILED DESCRIPTION

Figure 1:
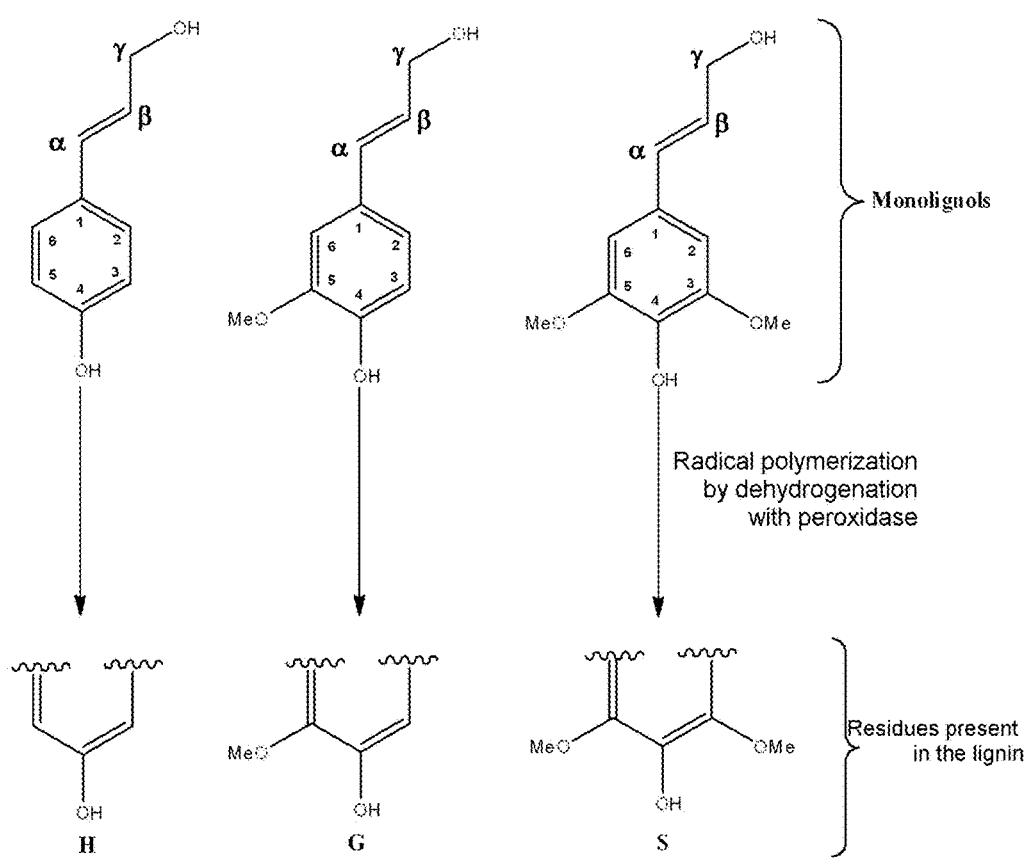
FIG. 1 illustrates the radical polymerization of three monomers called monolignols: p-coumarilyl alcohol, coniferyl alcohol and sinapyl alcohol, which, after polymerization by dehydrogenation with peroxidase, give respectively the p-hydroxyphenyl (H), guaiacyl (G) and syringyl (S) residues.
Figure 2:
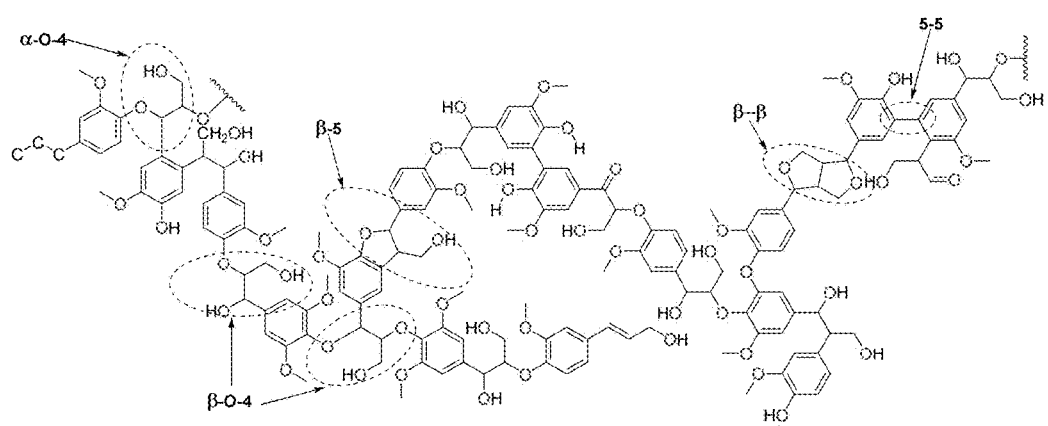
FIG. 2 shows the structure of lignin proposed by E. Adler, Wood Sci. Technol. 1977, 11, page 169.
Figure 4:
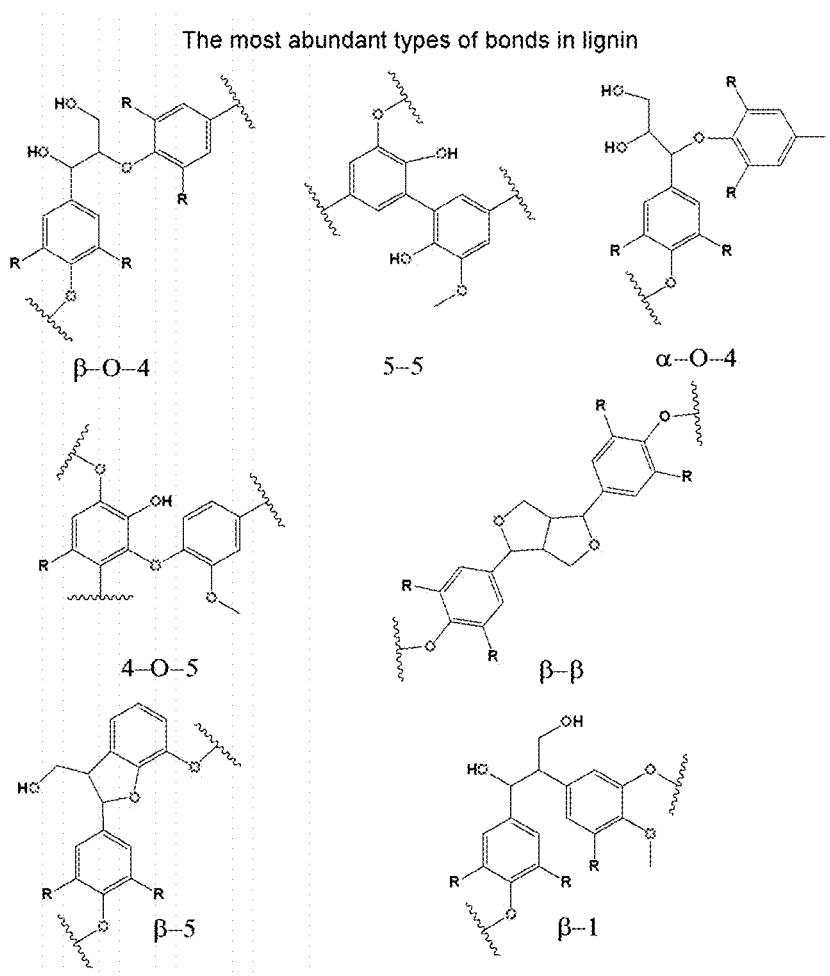
FIG. 4 shows the chemical structures of the most abundant types of bond present in lignin.
Figure 5:
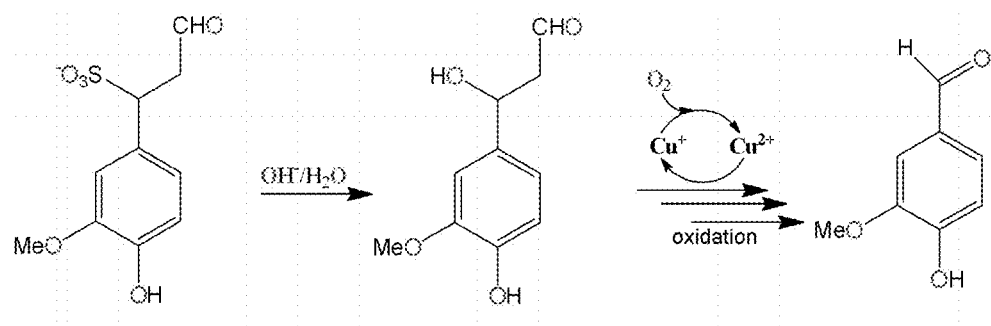
FIG. 5 illustrates a step in the process of preparing vanillin from lignosulfonate.

The process of the invention thus comprises a lignin depolymerization step. The lignin depolymerization allows selective cleavage of the carbon sp$^3$-oxygen bonds of the alkylaryl ethers present in the lignin and thus essentially targets the carbon sp$^3$-oxygen bonds of the β-O-4, α-O-4, β-5, β-1 and β-β type. Without wishing to be bound by any theory, the cleavage of the carbon sp$^3$-oxygen bonds at the level of the bonds of the β-O-4, α-O-4 and β-β type results in both the depolymerization of the lignin and the modification of its structure, whereas the cleavage of the carbon sp$^3$-oxygen bonds at the level of the bonds of the β-5 and β-1 type results in the modification of the structure of the lignin without cleavage of the bond between two successive monomers.

The carbon sp$^2$-oxygen bonds of the aryl ethers present in the lignin (especially the bonds of the 5-5 and 4-O-5 type) and also any other carbon sp$^2$-oxygen bond present in the lignin remain intact during the process of the invention.

The lignin depolymerization step in the process of the invention is carried out under mild operating conditions and makes it possible to dispense with the drastic temperature and pressure reaction conditions conventionally used in the literature for lignin depolymerization. The lignin depolymerization in the process of the invention is also industrially advantageous since it makes it possible to reduce costs by using silanes of formula (III) which are air-stable and inexpensive.

Moreover, the lignin depolymerization can generate methane and hydrogen (about from 7% to 20% by weight of the total weight of the lignin introduced). These two gases can optionally be used as fuels for supplying the process of the invention with energy.

In the depolymerization step, the silane compounds of formula (III) perform the cleavage by reduction of the carbon sp$^3$-oxygen bonds of the alkylaryl ethers present in the lignin, under catalytic conditions.

The process of the invention allows the preparation of the monocyclic aromatic compounds of formula (I) with good purity, that is to say a purity greater than or equal to 90% by weight, preferably of between 90% and 99.9% by weight, relative to the total weight of the monocyclic aromatic compounds of formula (I).

With the process of the invention, the monocyclic aromatic compounds of formula (I) can also be obtained as a mixture with oligomers made up of the monomeric entities bonded to one another by bonds that cannot be cleaved by the process of the invention, in particular C—C bonds and diaryl ether bonds. In this case, the monocyclic aromatic compounds of formula (I) can be easily purified by separation techniques well known to those skilled in the art and conventionally used in this field, for instance column chromatography, distillation, etc.

Indeed, contrary to the processes described in the literature, in the process of the invention, all the volatile products that may be formed continue to undergo reduction reactions so as to in the end give a single volatile product (principle of convergence), thereby facilitating their purification by distillation. Furthermore, given the fact that the products obtained are generally silylated, the boiling point of the product is decreased, thereby facilitating the distillation operating conditions. Moreover, since the by-products are non-volatile oligomers, they can be easily separated from the desired monocyclic aromatic product of formula (I) by distillation.

It should be noted that the monocyclic aromatic compounds of formula (I) obtained by means of the process of the invention can also be purified by column chromatography.

The monocyclic aromatic compounds of formula (I) generally have a weight-average molar mass of less than 2000 g/mol, preferably less than 1500 g/mol in silylated form (that is to say when all the —OH oxygen atoms of these —OH compounds are in —O—Si silylated form). After desilylation by hydrolysis for example, all the —O—Si bonds are cleaved and the weight-average molar mass of the monocyclic aromatic compounds of formula (I) in non-silylated form thus obtained is less than 450 g/mol, preferably less than 400 g/mol. The weight-average molar mass of the compounds obtained can be determined by any method known to those skilled in the art, in particular by size exclusion chromatography (SEC).

Moreover, the monocyclic aromatic compounds of formula (I) are obtained with a good yield (of from 10% to 70% by weight relative to the weight of the starting lignin, for example).

In the context of the present invention, the yield is defined as being the ratio of the weight of isolated aromatic compounds of formula (I), having a weight-average molar mass of less than 2000 g/mol, preferably less than 1500 g/mol for the compounds in silylated form or less than 450 g/mol, preferably less than 400 g/mol for the compounds in non-silylated form, to the weight of lignin initially introduced:

Yield=w(aromatic compounds of formula (I))/w (lignin)

w being the weight of the lignin initially introduced.

It should be noted that the determination of the exact amount of lignin is not easy. Ragauskas et al. (M. Nagy, K. David, G. J. P. Britovsek and A. J. Ragauskas, *Holzforschung,* 2009, 63, 513) describes an approximation of this amount which associates with each unit a molar mass of approximately 200 g/mol. In the light of the complexity and diversity of the structures of the lignins that are formed, having different proportions of H, G and S residues present in the lignins, and given the presence of several types of impurities having unknown structures, it is very difficult to determine a well-defined molecular formula for describing lignin. Consequently, the determination of the molar yield in the case of lignin is impossible, and the yields are expressed as weight of product obtained relative to the weight of lignin initially added.

For the purposes of the present invention, the term "alkyl" is intended to mean a linear, branched or cyclic, saturated, optionally substituted carbon-based radical comprising 1 to 12 carbon atoms, preferably 1 to 8 carbon atoms. By way of linear or branched, saturated alkyl, mention may be made for example of methyl, ethyl, propyl, butyl, pentyl, hexyl, octyl, nonyl, decyl, undecyl and dodecanyl radicals and branched isomers thereof. As cyclic alkyl, mention may be made of cyclopropyl, cyclobutyl, cyclopentyl, cyclohexyl, bicylco[2,1,1] hexyl and bicyclo[2,2,1] heptyl radicals.

The term "alkenyl" or "alkynyl" is intended to mean a linear, branched or cyclic, unsaturated, optionally substituted carbon-based radical, said unsaturated carbon-based radical comprising 2 to 12 carbon atoms, preferably 2 to 8 carbon atoms, comprising at least one double (alkenyl) or one triple bond (alkynyl). In this respect, mention may be made, for example, of ethylenyl, propylenyl, butenyl, pentenyl, hexenyl, acetylenyl, propynyl, butynyl, pentynyl and hexynyl radicals and branched isomers thereof. As unsaturated cyclic alkyls, mention may for example be made of cyclopentenyl and cyclohexenyl.

For the purposes of the invention, the alkyl, alkenyl and alkynyl groups can be optionally substituted with one or more hydroxyl groups; one or more alkoxy groups; one or more siloxy groups; one or more halogen atoms chosen from fluorine, chlorine, bromine and iodine atoms; one or more nitro (—NO$_2$) groups; one or more nitrile (—CN) groups; one or more aryl groups, with the alkoxy and aryl groups as defined in the context of the present invention.

The term "aryl" generally denotes a cyclic aromatic substituent comprising from 6 to 20, preferably from 6 to 12, carbon atoms. In the context of the invention, the aryl group may be monocyclic or polycyclic. By way of indication, mention may be made of phenyl, benzyl and naphthyl groups. The aryl group may be optionally substituted with one or more hydroxyl groups, one or more alkoxy groups, one or more "siloxy" groups, one or more halogen atoms chosen from fluorine, chlorine, bromine and iodine atoms, one or more nitro (—NO$_2$) groups, one or more nitrile (—CN) groups, one or more alkyl groups, with the alkoxy and alkyl groups as defined in the context of the present invention.

The term "heteroaryl" generally denotes a monocyclic or polycyclic aromatic substituent comprising from 5 to 10 members, preferably from 5 to 7 members, including at least 2 carbon atoms, and at least one heteroatom chosen from nitrogen, oxygen, boron, silicon, phosphorus and sulfur. The heteroaryl group may be monocyclic or polycyclic. By way of indication, mention may be made of furyl, benzofuranyl, pyrrolyl, indolyl, isoindolyl, azaindolyl, thiophenyl, benzothiophenyl, pyridyl, quinolinyl, isoquinolinyl, imidazolyl, benzimidazolyl, pyrazolyl, oxazolyl, isoxazolyl, benzoxazolyl, thiazolyl, benzothiazolyl, isothiazolyl, pyridazinyl, pyrimidilyl, pyrazinyl, triazinyl, cinnolinyl, phthalazinyl and quinazolinyl groups. The heteroaryl group may be optionally substituted with one or more hydroxyl groups, one or more alkoxy groups, one or more halogen atoms chosen from fluorine, chlorine, bromine and iodine atoms, one or more nitro (—NO$_2$) groups, one or more nitrile (—CN) groups, one or more aryl groups, one or more alkyl groups, with the alkyl, alkoxy and aryl groups as defined in the context of the present invention.

The term "alkoxy" signifies an alkyl, alkenyl and alkynyl group, as defined above, bonded by an oxygen atom (—O-alkyl, O-alkenyl, O-alkynyl).

The term "aryloxy" signifies an aryl group as defined above, bonded by an oxygen atom (—O-aryl).

The term "heterocycle" generally denotes a saturated or unsaturated, monocyclic or polycyclic substituent comprising from 5 to 10 members, preferably from 5 to 7 members, containing from 1 to 4 heteroatoms chosen, independently of one another, from nitrogen, oxygen, boron, silicon, phosphorus and sulfur. By way of indication, mention may be made of morpholinyl, piperidinyl, piperazinyl, pyrrolidinyl, imidazolidinyl, imidazolinyl, pyrazolidinyl, tetrahydrofuranyl, tetrahydropyranyl, thianyl, oxazolidinyl, isoxazolidinyl, thiazolidinyl and isothiazolidinyl substituents. The heterocycle may be optionally substituted with one or more hydroxyl groups, one or more alkoxy groups, one or more aryl groups, one or more halogen atoms chosen from fluorine, chlorine, bromine and iodine atoms, one or more nitro (—NO$_2$) groups, one or more nitrile (—CN) groups, one or more alkyl groups, with the alkyl, alkoxy and aryl groups as defined in the context of the present invention.

The term "halogen atom" is intended to mean an atom chosen from fluorine, chlorine, bromine and iodine atoms.

The term "silylated" group is intended to mean a group of formula [—Si(X)$_3$] in which X, independently of one another, is chosen from a hydrogen atom; one or more halogen atoms chosen from fluorine, chlorine, bromine or iodine atoms; one or more alkyl groups; one or more alkoxy groups; one or more aryl groups; one or more siloxy groups; with the alkyl, alkoxy, aryl and siloxy groups as defined in the context of the present invention. When at least one of the X represents several siloxy groups, said siloxy groups can be repeated several times so as to produce polymeric organosilanes of general formula

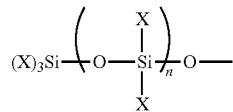

in which X is as defined above and n is an integer between 1 and 20 000, advantageously between 1 and 5000, more advantageously between 1 and 1000. In this respect, mention may for example be made of polydimethylsiloxane (PDMS), polymethylhydroxysiloxane (PMHS) and tetramethyldisiloxane (TMDS).

The term "siloxy" group is intended to mean a silylated group, as defined above, bonded by an oxygen atom (—O—Si(X)$_3$) with X as defined above.

Figure 6:
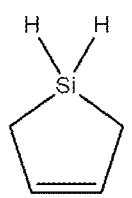
FIG. 6 shows the structures of 1-silacyclo-3-pentene and 1-methyl-1,1-dihydrido-2,3,4,5-tetraphenyl-1-silacyclopentadiene.
Figure 6:
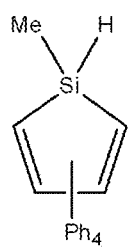

For the purposes of the invention, the term "silylated heterocycle" is intended to mean a saturated or unsaturated, monocyclic or polycyclic substituent comprising from 5 to 15 members, preferably from 5 to 7 members, containing at least one silicon atom and optionally at least one other heteroatom chosen from nitrogen, oxygen and sulfur. Said silylated heterocycle may be optionally substituted with one or more hydroxyl groups; one or more alkyl groups, one or more alkoxy groups; one or more halogen atoms chosen from fluorine, chlorine, bromine and iodine atoms; one or more aryl groups, with the alkyl, alkoxy and aryl groups as defined in the context of the present invention. Among the silylated heterocycles, mention may for example be made of 1-silacyclo-3-pentene or 1-methyl-1,1-dihydrido-2,3,4,5-tetraphenyl-1-silacyclopentadiene, according to the formulae of FIG. 6.

Figure 7:
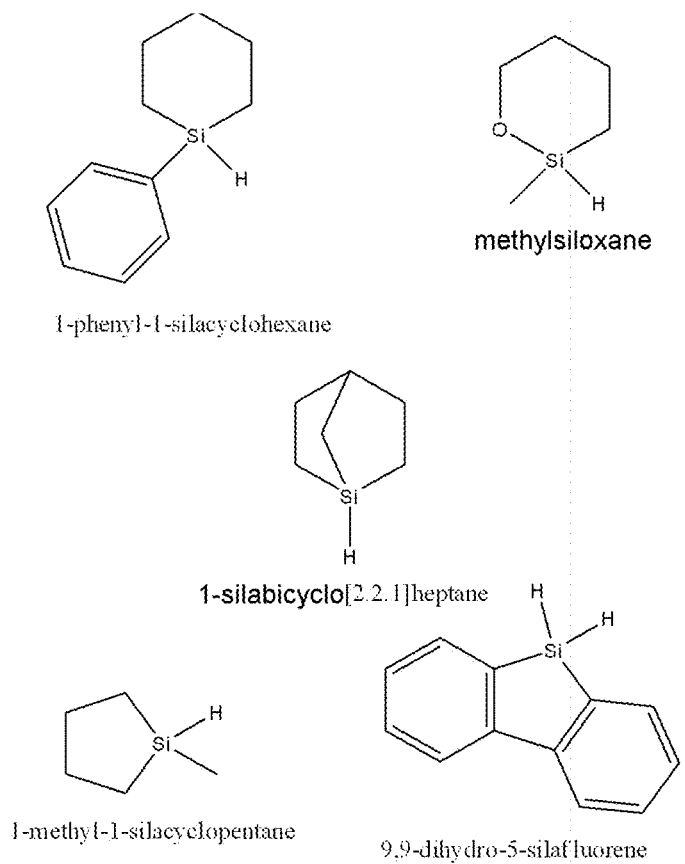
FIG. 7 shows the structures of methylsiloxane, 1-phenyl-1-silacyclohexane, 1-silabicyclo[2.2.1]heptane, 1-methyl-1-silacyclopentane, and 9,9-dihydro-5-silafluorene.

Mention may also be made, for example, of methylsiloxane, 1-phenyl-1-silacyclohexane, 1-silabicyclo[2.2.1]heptane, 1-methyl-1-silacyclopentane, and 9,9-dihydro-5-silafluorene corresponding to the formulae of FIG. 7.

The term "polyol" is intended to mean: an organic compound characterized by the presence of a certain number of hydroxyl (—OH) groups. In the context of this invention, a polyol compound contains at least one hydroxyl group. For this, the term "polyol" is intended to mean a compound of formula Z—(OH)$_n$ in which n is greater than or equal to 1, and Z is chosen from one or more alkyl groups, one or more alkoxy groups, one or more siloxy groups, one or more aryl groups, and one or more heteroaryl groups with the alkyl, alkoxy and aryl groups being as defined in the context of the present invention.

The term "amino" group is intended to mean a group of formula —NR$^8$R$^9$, in which:

R$^8$ and R$^9$ represent, independently of one another, a hydrogen atom, an alkyl group, an alkenyl group, an alkynyl group, an aryl group, a heteroaryl group, a heterocycle, a silylated group or a siloxy group, with the alkyl, alkenyl, alkynyl, aryl, heteroaryl, heterocycle, silylated and siloxy groups as defined in the context of the present invention; or R$^8$ and R$^9$, taken together with the nitrogen atom to which they are bonded, form a heterocycle optionally substituted with one or more hydroxyl groups; one or more alkyl groups; one or more alkoxy groups; one or more halogen atoms chosen from fluorine, chlorine, bromine and iodine atoms; one or more nitro (—NO$_2$) groups; one or more nitrile (—CN) groups; one or more aryl groups; with the alkyl, alkoxy and aryl groups as defined in the context of the present invention.

The term "wood" is intended to mean a plant tissue which corresponds to the secondary xylem in plants. The term "wood" encompasses all the secondary tissues forming the trunks, branches and roots of ligneous plants.

The term "gymnosperms" is intended to mean plants belonging to the paraphyletic sub-branch of the spermatophytes (seed plants) and including the plants of which the ovule is naked and is born by foliar parts grouped on a fertile branch (the cone). Most gymnosperms belong to the conifer (or pinophyta) division.

The term "angiosperms" is intended to mean plants belonging to the paraphyletic sub-branch of the spermatophytes (seed plants) and including flowering plants, and thus fruit-bearing plants. These plants constitute the largest part of the terrestrial plant species with 250 000 to 300 000 species.

The term "Pinaceae" or "Abietaceae" is intended to mean a family of gymnosperm plants and more specifically of the conifer division which contains between 220 and 250 species divided up into 11 genera. They are trees or shrubs, which have evergreen needle-shaped or scale leaves or deciduous leaves.

The term "lignin" is intended to mean a biopolymer present in all plants and mainly in vascular plants, ligneous plants, herbaceous plants and algae. Lignin constitutes one of the main components of wood. Lignin is a polyol rich in aryl groups as defined above. It is derived from a plant tissue, in particular from leaves, from herbaceous stalks and ligneous stalks. Depending on the process for extracting it and its origin, lignin can contain other chemical groups, for instance alkenes, alkynes, primary, secondary and tertiary alcohols, ketones, carboxylic acids, acetals, hemiacetals, enols, ethers, esters, allyl alcohols, homoallyl alcohols, nitriles, imines, primary, secondary and tertiary amines, amides, halogens, sulfides, thiols, sulfonates, sulfones, sulfates and sulfoxides.

Preferably, the process of the invention makes it possible to prepare a monocyclic aromatic compound of formula (I) in which R$^1$, R$^2$ and R$^3$ represent, independently of one another, a hydrogen atom; a hydroxyl group; an alkoxy group of which the alkyl group is chosen from methyl, ethyl, propyl and butyl groups and branched isomers thereof; a siloxy (—O—Si(X)$_3$) group in which each X, independently of one another, is chosen from a hydrogen atom, an alkyl group chosen from methyl, ethyl and propyl groups, an aryl group chosen from phenyl and benzyl, a polymeric organosilane of general formula

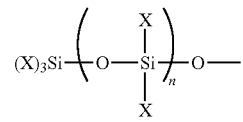

in which X is as defined above and n is an integer between 1 and 20 000, advantageously between 1 and 5000, more advantageously between 1 and 1000;

Y represents an alkyl group chosen from methyl, ethyl, propyl groups and butyl groups and branched isomers thereof; a carbonyl —CR$^4$=O group with R$^4$ representing a hydrogen atom; an alkyl group chosen from methyl, ethyl, propyl and butyl groups and branched isomers thereof; and a hydroxyl group;

said alkyl groups being optionally substituted with one or more hydroxyl groups; one or more siloxy (—O—Si(X)$_3$) groups in which each X, independently of one another, is chosen from a hydrogen atom, an alkyl group chosen from methyl, ethyl and propyl groups, an aryl group chosen from phenyl and benzyl, a polymeric organosilane of general formula

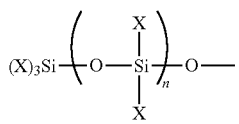

in which X is as defined above and n is an integer between 1 and 20 000, advantageously between 1 and 5000, more advantageously between 1 and 1000.

More preferentially, the process of the invention makes it possible to prepare a monocyclic aromatic compound of formula (I) in which $R^1$, $R^2$ and $R^3$ represent, independently of one another, a hydrogen atom; a hydroxyl group; an alkoxy group of which the alkyl group is a methyl group or an ethyl group; a siloxy (—O—Si$(X)_3$) group in which each X, independently of one another, is a hydrogen atom, a methyl group, an ethyl group, a phenyl group, polydimethylsiloxane (PDMS), polymethylhydroxysiloxane (PMHS) or tetramethyldisiloxane (TMDS);

Y represents an alkyl group chosen from methyl, ethyl, propyl and butyl groups and branched isomers thereof; a carbonyl —C$R^4$=O group with $R^4$ representing a hydrogen atom; an alkyl group chosen from methyl, ethyl, propyl and butyl groups and branched isomers thereof; and a hydroxyl group;

said alkyl groups being optionally substituted with one or more hydroxyl groups; one or more siloxy (—O—Si$(X)_3$) groups in which each X, independently of one another, is chosen from a hydrogen atom, a methyl group, an ethyl group, a phenyl group, polydimethylsiloxane (PDMS), polymethylhydroxysiloxane (PMHS) and tetramethyldisiloxane (TMDS).

Preferably, the depolymerization step uses a silane compound of formula (III) in which $R^5$, $R^6$ and $R^7$ represent, independently of one another, a hydrogen atom; an alkyl group chosen from methyl, ethyl, propyl and butyl groups and branched isomers thereof; a siloxy (—O—Si$(X)_3$) group in which each X, independently of one another, is an alkyl group chosen from methyl, ethyl, propyl and butyl groups and branched isomers thereof; an alkoxy group of which the alkyl group is chosen from methyl, ethyl, propyl and butyl groups and branched isomers thereof; an aryl group chosen from phenyl and benzyl groups; said alkyl and aryl groups being optionally substituted.

More preferably, in the silane compound of formula (III), $R^5$, $R^6$ and $R^7$ represent, independently of one another, a hydrogen atom; an alkyl group chosen from methyl, ethyl and propyl groups; or an aryl group chosen from benzyl and phenyl groups.

In the process of the invention, it is essential for the lignin used in the depolymerization step to be free of sulfur, that is to say it contains a sulfur content of less than 1.5% by weight relative to the total weight of the lignin. This is because the inventors have observed, entirely unexpectedly, that when lignin contains a sulfur content greater than or equal to 1.5% by weight relative to the total weight of the lignin, the depolymerization of the lignin does not take place or is partial. When the depolymerization is partial, it results in molecules having a weight-average molar mass of greater than 2000 g/mol for the molecules in silylated form. The sulfur content of the lignin used in the process of the invention is thus advantageously greater than or equal to zero and remains less than 1.5% by weight, relative to the total weight of the lignin, as defined below:

0≤sulfur content of the lignin<1.5% by weight, relative to the total weight of the lignin.

In the depolymerization step, the reaction between the lignin and the silane compound of formula (III) takes place in the presence of a catalyst.

For the purposes of the invention, the term "catalyst" is intended to mean any compound capable of modifying, in particular by increasing, the rate of the chemical reaction in which it participates, and which is regenerated at the end of the reaction. This definition encompasses both the catalysts, that is to say the compounds which exercise their catalytic activity without needing to undergo any modification or conversion, and the compounds (also called precatalyst) which are introduced into the reaction medium and which are converted into a catalyst in said reaction medium.

It is in particular necessary for the catalyst to be chosen while taking into account in particular its steric hindrance, its ability to activate the silane and its solubility in the reaction medium.

In the depolymerization step of the process of the invention, the catalyst may be an organic catalyst chosen from:

carbocations of formula $(X^1)_3C^+$ with $X^1$ representing a hydrogen atom, an alkyl group, an aryl group, an alkoxy group, a silyl group, a siloxy group and a halogen atom, as defined above, said carbocations being chosen from the trityl cation (($C_6H_5)_3C^+$), tropilium $(C_7H_7)^+$, the benzyl cation $(C_6H_5CH_2^+)$, the allyl cation (CH$_3$—CH$^+$—CH=CH$_2$), methylium (CH$_3^+$), cyclopropylium $(C_3H_5^+)$, the cyclopropyl carbocation of formula C$_3$H$_5$—C$^+$R$^1$R$^2$ with R$^1$ and R$^2$ as defined above, said cyclopropyl carbocation being chosen from the dimethylcyclopropyl carbocation and the dicyclopropyl carbocation, the triazabicyclodecene (TBD) cation, acylium (R$^1$—C=O)$^+$ with R$^1$ as defined above and chosen from methyl, propyl and benzyl, benzenium $(C_6H_5)^+$, and the norbornyl $(C_7H_{11})^+$ cation;

oxoniums chosen from (CH$_3$)$_3$O$^+$BF$_4^-$ (Meerwein salt) and (CH$_3$CH$_2$)$_3$O$^+$BF$_4^-$;

a silylium ion (R$^5$)$_3$Si$^+$ with R$^5$ as defined previously, for example chosen from Et$_3$Si$^+$ and Me$_3$Si$^+$;

disilyl cations, preferably disilyl cations having a bridging hydride, chosen from the formulations indicated below

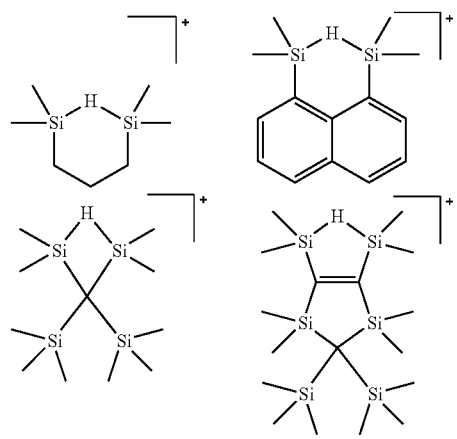

The carbocations mentioned above are commercial or can be easily synthesized by those skilled in the art by means of various synthesis processes, for example: cation pool process, the internal redox process, the process using a leaving group, processes using Lewis or Bronsted acids. These processes are described in the following references: R. R. Naredla and D. A. Klumpp, *Chem. Rev.* 2013, 113, pages 6905-6948; M. Saunders and H. A. Jimenez-Vazquez, *Chem. Rev.* 1991, 91, pages 375-397.

It should be noted that the anionic counterion of the silylium ion, of the carbocations and of the disilyl cations mentioned above is preferably a halide chosen from $F^-$, $Cl^-$, $Br^-$ and $I^-$, or an anion chosen from $BF_4^-$, $SbF_6^-$, $B(C_6F_5)_4^-$, $B(C_6H_5)_4^-$, $TfO^-$ or $CF_3SO_3^-$, $PF_6^-$.

In the process of the invention, the catalyst may also be organometallic. In this respect, mention may be made of the iridium complexes of formula (IV)

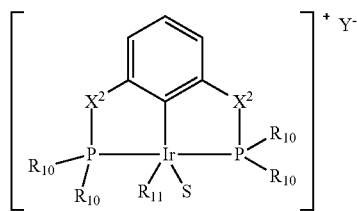

(IV)

in which $R^{10}$ represents an alkyl or aryl group as defined previously, and preferably a tert-butyl group;

$R^{11}$ represents a hydrogen atom or an alkyl group as defined above, and preferably a hydrogen atom;

$X^2$ represents a —$CH_2$— group or an oxygen atom, and preferably an oxygen atom;

$Y^-$ represents a counterion chosen from $B(C_6F_5)_4^-$ and $B(C_6H_5)_4^-$, and preferably $B(C_6F_5)_4^-$; and S represents a solvent molecule, coordinated to be complex, chosen from dimethyl sulfoxide (DMSO), acetonitrile ($CH_3CN$) and acetone ($CH_3COCH_3$), and preferably acetone.

Preferably, the iridium catalyst is [(POCOP)Ir(H)(acetone)]$^+$B($C_6F_5$)$_4^-$ with (POCOP) representing 2,6-bis(di-tert-butylphosphinito)phenyl. This catalyst can be prepared according to the processes described by I. Gottker-Schnetmann, P. White, and M. Brookhart, *J. Am. Chem. Soc.* 2004, 126, pages 1804-1811; and by J. Yang and M. Brookhart, *J. Am. Chem. Soc.* 2007, 129, pages 12656-12657.

In the process of the invention, the catalyst may also be organometallic. In this respect, mention may be made of the ruthenium complexes of formula (V)

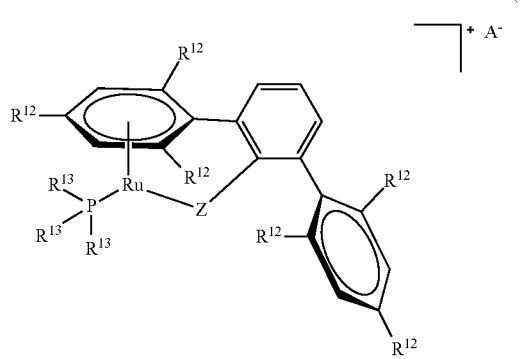

(V)

in which $R^{12}$ represents a hydrogen atom or an alkyl group as defined previously, $R^{12}$ preferably being a methyl group;

$R^{13}$ represents an aryl group or an alkyl group as defined previously, said aryl and alkyl groups being optionally substituted, $R^{13}$ preferably being p-FC$_6$H$_4$;

Z represents a —$CH_2$— group, an oxygen atom or a sulfur atom, Z preferably being a sulfur atom; and $A^-$ represents a counterion chosen from $B(C_6F_5)_4^-$ and $[CHB_{11}H_5Cl_6]^-$, $A^-$ preferably being $B(C_6F_5)_4^-$.

This type of catalyst can be prepared according to the processes described by T. Stahl, H. F. T. Klare, and M. Oestreich, *J. Am. Chem. Soc.*, 2013, 135, pages 1248-1251.

The catalyst may also be of Lewis acid type chosen from organometallic and metallic catalysts. The organometallic and metallic catalysts are chosen from:

boron compounds of formula $B(X^3)_3$ with $X^3$ representing a hydrogen atom, an alkyl group, an aryl group or an alkoxy group, as defined previously, said boron compounds being chosen from $BF_3$, $BF_3(Et_2O)$, $BCl_3$, $BBr_3$, triphenyl hydroborane, tricyclohexyl hydroborane, $B(C_6F_5)_3$, B-methoxy-9-borabicyclo[3.3.1]nonane (B-methoxy-9-BBN) and B-benzyl-9-borabicyclo[3.3.1]nonane (B-benzyl-9-BBN);

borenium compounds $R^1R^2B^+$ with $R^1$ and $R^2$ as defined previously, for example $R^1=R^2=$phenyl and $R^1=R^2=$methylene (Y. Shoji, N. Tanaka, K. Mikami, M. Uchiyama and T. Fukushima, Nat. Chem., 2014, 6, 498-503), said borenium compounds being for example Me-TBD-BBN$^+$, the borenium ferrocene derivatives corresponding to the formula

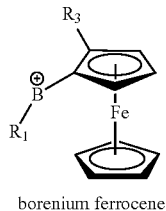

borenium ferrocene in which $R^1$ and $R^3$ are as defined previously, for example $R^1=$phenyl and $R^3=$3,5-dimethylpyridyl (J. Chen, R. A. Lalancettea and F. Jakle, *Chem. Commun.*, 2013, 49, pages 4893-4895);

aluminum compounds chosen from $AlCl_3$, $AlBr_3$, aluminum isopropoxide $Al(O-i-Pr)_3$, aluminum ethanoate ($Al(C_2H_3O_2)$), the Krossing salt [Ag(CH$_2$Cl$_2$)]{Al[OC(CF$_3$)$_3$]$_4$}, Li{Al[OC(CF$_3$)$_3$]}, and cationic aluminum compounds of formula $(X^4)_2Al^+$ with $X^4$ being a halogen atom, an alkoxy group or an alkyl group, as defined previously for instance $Et_2Al^+$;

indium compounds chosen from $InCl_3$ and $In(OTf)_3$;

iron compounds chosen from $FeCl_3$ and $Fe(OTf)_3$;

tin compounds chosen from $SnCl_4$ and $Sn(OTf)_2$;

phosphorus compounds chosen from $PCl_3$, $PCl_5$ and $POCl_3$;

trifluoromethanesulfonate or triflate ($CF_3SO_3^-$) compounds of transition metals and lanthanides chosen from scandium triflate, ytterbium triflate, yttrium triflate, cerium triflate, samarium triflate and niodinium triflate.

In the context of the present invention, OTf$^-$ represents the triflate or trifluoromethanesulfonate ion of formula $CF_3SO_3^-$; the terms triflate or trifluoromethanesulfonate, OTf⁻ or $CF_3SO_3^-$ can thus be used without distinction to denote the same entity.

The preparation of the borenium ferrocene derivatives is described by J. Chen, R. A. Lalancettea and F. Jakle, *Chem. Commun.*, 2013, 49, pages 4893-4895; the preparation of the Krossing salts is described by I. Krossing, *Chem.-Eur. J.*, 2001, 7, page 490; and the preparation of $Et_2Al^+$ is described by M. Khandelwal and R. J. Wehmschulte, *Angew. Chem. Int. Ed.* 2012, 51, pages 7323-7326.

Preferably, the catalyst is an organometallic catalyst chosen from $BF_3$; $InCl_3$; and triphenylcarbenium tetrakis(perfluorophenyl)borate $[(Ph)_3C^+B(C_6F_5)_4]^-$.

Figure 8:
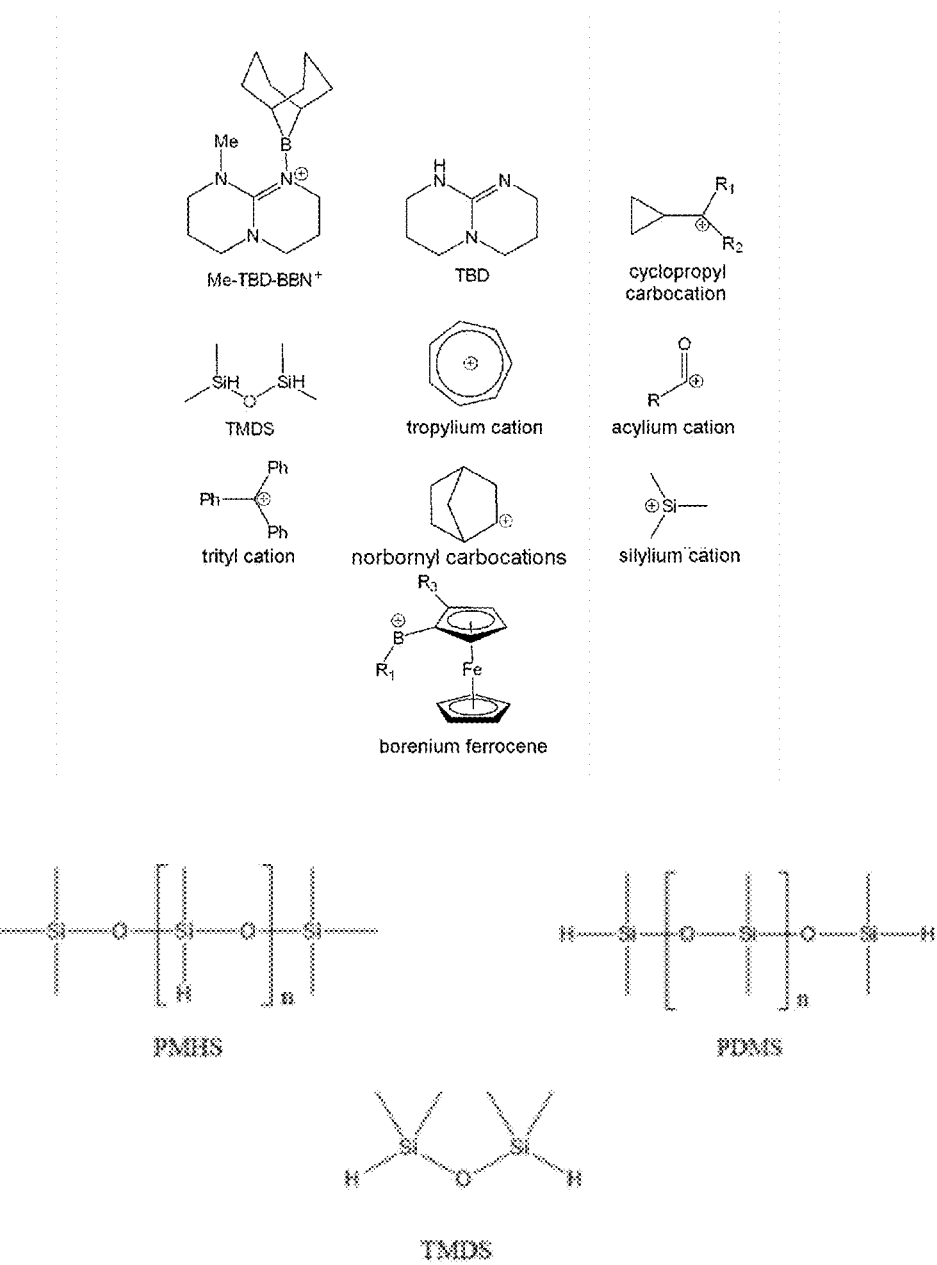
FIG. 8 shows structures and corresponding abbreviations of various catalyst.

Some of the abbreviations used in the context of the invention are represented in FIG. 8.

The catalysts may, where appropriate, be immobilized on heterogeneous supports in order to ensure easy separation of said catalyst and/or recycling thereof. Said heterogeneous supports can be chosen from supports based on silica gel and on plastic polymers, for instance polystyrene; carbon supports chosen from carbon nanotubes; silica carbide; alumina; and magnesium chloride ($MgCl_2$).

In the depolymerization step of the process according to the invention, the reaction can take place under a pressure of a or of a mixture of inert gas(es) chosen from nitrogen and argon, or of gases generated by the process, in particular methane and hydrogen. The pressure can be between 0.2 and 50 bar, preferably between 0.2 and 30 bar, more preferentially between 1 and 20 bar, limits included.

The temperature of the reaction can be between 0 and 150° C., preferably between 0 and 125° C., more preferentially between 25 and 70° C., limits included.

The reaction time depends on the degree of conversion of the silane compound of formula (III), on the nature of the lignin and also on the desired degree of silylation.

The reaction can be carried out for a period of from 1 minute to 200 hours, advantageously from 1 minute to 48 hours, preferably from 10 minutes to 48 hours, limits included.

In the depolymerization step, in particular the reaction between the various reagents, can take place in a or a mixture of at least two solvent(s) chosen from:
  silylated ethers, preferably chosen from 1,1,1,3,3,3-hexamethyldisiloxane (($Me_3Si)_2O$) and 1,1,1,3,3,3-hexaethyldisiloxane (($Et_3Si)_2O$);
  hydrocarbons, preferably chosen from benzene, toluene, pentane and hexane;
  sulfoxides, preferably chosen from dimethyl sulfoxide (DMSO);
  alkyl halides, preferably chosen from chloroform, methylene chloride, chlorobenzene and dichlorobenzene.

The silanes of formula (III) and the catalysts used in the depolymerization step are generally commercial compounds or can be prepared by means of processes known to those skilled in the art.

The weight ratio between the silane compound of formula (III) and the lignin depends on the type of lignins used and on the type of final molecules desired (obtaining of optionally silylated primary alcohols of the type IIb, IId, IIf or obtaining of silylated ethers of the type IIa, IIc, IIe, as represented in the examples). The compounds of formula (II) containing an unsubstituted propyl chain are the products of reduction of compounds comprising aliphatic siloxy groups. The reduction of these silylated alcohols to alkanes is carried out by the same process as that which is used for the depolymerization of the lignin. Since the depolymerization process reduces carbon sp3-oxygen bonds, the silylated bonds (—C—O—Si—) can be easily reduced to alkane (—C—H) or to alcohol (—C—OH). The alcohol/alkane selectivity will depend on the number of equivalents of silane compound of formula (III) added.

Thus, in the context of the present invention, the weight ratio between the silane compound of formula (III) and the lignin can be between 0.5 and 6, preferably between 1 and 4, limits included.

The amount of catalyst used in the depolymerization step is from 0.001 to 1 weight equivalent, preferably from 0.001 to 0.9 weight equivalent, more preferentially from 0.01 to 0.9 weight equivalent, even more preferentially from 0.01 to 0.5 weight equivalent, limits included, relative to the initial weight of the lignin.

After the depolymerization, the resulting aromatic compounds may be in silylated form. Simple hydrolysis under conditions well known to those skilled in the art can then result in the corresponding aromatic compounds in their non-silylated forms.

In the context of the present invention, the term "hydrolysis" is intended to mean a process for converting the siloxy groups present in silylated aromatic compounds derived from lignin depolymerization, into hydroxyl groups, by means of a desilylation reaction. This conversion can be carried out under acidic or basic conditions or else in the presence of fluoride ions, these conditions being well known to those skilled in the art. In the context of the present invention, the hydrolysis process is preferably chosen from: 2 M HCL or $H_2SO_4$ in THF; 10% NaOH or KOH in a water/THF mixture; and 1 M tetra-n-butylammonium fluoride (TBAF) in THF.

A simple filtration can make it possible to recover the optionally supported catalyst and to remove any by-products.

As already indicated, the process of the invention allows the preparation of the monocyclic aromatic compounds of formula (I) with good purity, that is to say a purity of greater than or equal to 90% by weight, preferably of between 90% and 99.9% by weight, relative to the total weight of the monocyclic aromatic compounds of formula (I), or which can be easily purified. In the case where purification of the monocyclic aromatic compounds of formula (I) proves to be necessary, separation techniques well known to those skilled in the art and conventionally used in this field, for instance distillation or column chromatography, can be implemented.

In the process of the invention, the choice of the plant species from which the lignin will be extracted and also the process for the extraction thereof plays an important role, in particular regarding the nature of the aromatic compound of formula (I) that it has been sought to obtain and thus the selectivity of the process of the invention, regarding the yield of the process of the invention, regarding the degree of purity of said aromatic compound and regarding the productivity of the depolymerization step. The more the percentage of residue capable of giving the desired molecule increases in the species, the more the productivity of the process increases.

The plant species is selected by taking into account the parameters described hereinafter.
a) The plant species selected must advantageously contain a relatively high percentage, that is to say at least 10% by weight, of lignin relative to the total weight of the sample of the selected plant species, this being in order to increase the overall yield of final monocyclic aromatic compound of formula (I) relative to the starting material, for example wood.

b) The plant species must be selected so as to have at least 50% of G, H or S residue relative to the total number of residues present in the lignin used. It should be noted that the percentage of the residues present in the lignin can be determined by techniques known to those skilled in the art, for example pyrolysis, NMR, etc. This parameter plays an important role in the selectivity with respect to the monocyclic aromatic compound of formula (I) that will be obtained and also in the increase in the yield of said aromatic compound. As already indicated, lignin contains p-hydroxyphenyl (H), guaiacyl (G) and syringyl (S) residues. However, the complexity and also the structure of lignin depends greatly on its origin. In point of fact, using the lignin classification as a basis, it is possible to identify four types: G, GS, HGS and HG.

The G type can be distinguished from the others given that the species containing this type of lignin are exclusively made up of G-type residues. This type of lignin is generally derived from gymnosperms (softwood) and more specifically from the conifer (Pinophyta) division which is made up of 600-650 plant species.

For the other types of residues, the natural species always contain GS or HG mixtures, and the lignins derived from these species are characterized by the S/G or H/G ratio. However, there are species which may be rich in S or H residue. By way of example, mention may be made of common eucalyptus (*Eucalyptus globulus*) (hardwood) which has an S/G ratio of 6.

There are also plant species that have been genetically modified so as to preferentially have a very major single residue. For example, Mansfield went from an S/G ratio=2 to an S/G ratio=12 for poplar (J. J. Stewart, T. Akiyama, C. Chapple, J. Ralph, and S. D. Mansfield, *Plant Physiol.* 2009, 150, pages 621-635). It should be noted that, even if these ratios between the residues are not adhered to, for example in the case where a mixture of residue is contained in the species, the productivity will decrease but it will be possible to separate the final products by a method known to those skilled in the art, for example distillation or column chromatography.

c) The species must likewise be advantageously selected so as to maximize, that is to say have at least 30% of, cleavable bonds relative to the total number of bonds present between the monomer units in the lignin. For the purposes of the invention, the term "cleavable bonds" is intended to mean carbon $sp^3$-oxygen bonds which may be cleaved by the depolymerization step and which result in the cleavage of all the connections between two successive monomer units present in the lignin. In the context of the present invention, the selective cleavage of the carbon $sp^3$-oxygen bonds targets the bonds of β-O-4 and α-O-4 types. In the process of the invention, the lignin used may for example be a lignin containing at least 30% of bonds of the β-O-4 type and at least 3% α-O-4 bonds. In the case of wood lignin, the bonds of β-O-4 and α-O-4 types constitute between 40% and 60% of the bonds present. The percentages indicated correspond to the percentage of one type of bond relative to the total number of bonds present between the monomer units in the lignin. This percentage can be determined by NMR or pyrolysis, for example.

Lignin also comprises bonds that are modifiable but not cleavable, for instance β-5, β-1 and β-β bonds. The lignin depolymerization step in the process of the invention modifies these bonds, but a link is always conserved between the aromatic monomers of the lignin.

Finally, the third category of bond groups together the non-cleavable and non-modifiable bonds, for instance 4-O-5 and 5-5 bonds. In the context of the present invention, these bonds are inert and remain intact under the operating conditions applied. It is thus important to select a lignin with as many cleavable bonds as possible (at least 30% of cleavable bonds relative to the total number of bonds present between the monomer units in the lignin) so as to be able to carry out a successful depolymerization of the lignin into fragments similar to the starting monolignols as shown in FIG. 1.

Preferably, in the process of the invention, prior to the lignin depolymerization step, the plant species from which the lignin originates is selected. The plant species is preferably selected so as to increase the β-O-4 and α-O-4 cleavable bonds and so as to have a predominant H, G or S residue type in the lignin.

Thus, the plant species is preferably selected so as to have:
at least 10% by weight of lignin relative to the total weight of the sample of the plant species selected;
at least 30% of cleavable bonds relative to the total number of bonds present between the monomer units in the lignin; and
at least 50% of G, H or S residue relative to the total number of residues present in the lignin used.

The plant species can be chosen, for example, from
cedars, pines, spruces and firs for targeting the formation of a monocyclic aromatic compound of formula (I) having a structure derived from the G unit; or
poplars, oaks and eucalyptuses for the purpose of generating a monocyclic aromatic compound of formula (I) having a structure derived from the S unit.

Once the plant species has been selected, it must be treated so as to extract the lignin. For the purposes of the invention, the lignin extraction process denotes any physical and chemical technique making it possible to extract, isolate, separate and prepare the lignin. By way of example, mention may be made of the kraft process (producing kraft lignin), the sulfite process (producing lignosulfonates), the Organosolv processes which correspond to processes using one or more organic solvents for extracting the lignin (i.e. the processes: Acetocell, Alcell, Acetosolv, ASAM, Organocell, Milox, Formacell, Batelle/Geneva phenol), the steam-explosion process, the Klason process, the soda-AQ process (producing soda lignin or alkaline lignin), the lignin biological extraction process using biological organisms such as bacteria and enzymes, and the lignin extraction process by acid hydrolysis.

The Organosolv processes are described by the following references:
a) Alcell: J. H. Lora, W. G. Glasser, *J Polym Environ,* 2002, 10, 39-48;
b) Acetocell: Bojan Jankovic, *Bioresource Technol.,* 2011, 102, 9763-9771;
c) Acetosolv: J. C. Parajo, J. L. Alonso, D. Vazquez, *Bioresource Technology,* 1993, 46, 233-240;
d) ASAM: I. Miranda, H. Pereira, *Holzforschung,* 2002, 56, 85-90;
e) Batelle/Genevaphenol: A. Johansson, O. Aaltonen, P. Ylinen, *Biomass* 1987, 13, 45-65;
f) Formacell: X. F. Sun, R. C. Sun, P. Fowler, M. S. Baird, *Carbohydr. Polym.,* 2004, 55, 379-391;
g) Milox: P. Ligero, A. Vega, J. J. Villaverde, *Bioresource Technol.,* 2010, 101, 3188-3193;
h) Organocell: A. Lindner, G. Wegener, *J. Wood Chem. Technol.* 1988, 8, 323-340.

In the case of wood, the abovementioned extraction processes allow the separation of the three main constituents of wood: cellulose, hemicellulose and lignin. The abovementioned processes are mainly based on chemical or thermochemical conversions, thereby resulting in modification of the structure of the lignin extracted. This means that a wood derived from one and the same species can generate various lignin structures, this being dependent on the extraction process used.

In the context of the present invention, the lignin extraction process is chosen so as to modify as little as possible the structure of the initial lignin present in the species.

Thus, the lignin derived from the extraction process keeps the same types of functionalities and the same proportions of bonds as those present in the starting lignin. This contributes to increasing the overall yield of the process of the invention and also the selectivity with respect to a given monocyclic aromatic compound of formula (I). The extraction process in the present invention is preferably chosen from the processes of Organosolv types which make it possible to obtain lignins of which the structure is very close to that of the initial lignin present in the species.

In the context of the invention, the lignin extraction process can also encompass the processes for treating the lignin with the aim of introducing chemical functionalizations, of changing the physical properties and/or modifying the average molar mass of the lignin. Lignin is a polymer formed by a distribution of polymeric fragments having various molar masses. The average molar mass of lignin thus corresponds to the average of the masses of these polymeric fragments; it can be calculated relative to the mass of the fragments or relative to their number. These treatment processes can improve the yield and the selectivity of the process of the invention. Thus, at the end of the abovementioned extraction processes, the lignin can be treated in order to modify the ratio of the H, G and S residues of which it is constituted. This modification can thus, in certain cases, result in an enrichment with a given residue and/or with a given type of bond, and subsequently in increasing the selectivity and also the yield and reducing the purification steps resulting in the final monocyclic aromatic compound. It should be noted that lignins which have been functionalized at the end of their extraction (for example the kraft lignin and lignosulfonates) can, after a defunctionalization reaction (for example, a desulfurization reaction), be used in the process of the invention in order to result selectively in a pure monocyclic aromatic compound, that is to say having a purity of greater than or equal to 90% by weight, preferably of between 90% and 99.9% by weight, relative to the total weight of the monocyclic aromatic compounds of formula (I).

As already indicated, whatever the process used to extract and/or treat the lignin, it is essential for the lignin obtained to be free of sulfur, that is to say for it to contain a sulfur content of less than 1.5% by weight, relative to the total weight of the lignin. The sulfur content of the lignin used in the process of the invention is thus advantageously greater than or equal to zero and remains less than 1.5% by weight, relative to the total weight of the lignin.

The sulfur content can be determined by physical and chemical techniques known to those skilled in the art, for instance elemental analysis, or titration by ion chromatography, by infrared spectrophotometry, by oxidation of the sulfur to $SO_2$ followed by a titration of the latter using techniques known to those skilled in the art, for instance acidimetric titration, iodometric titration or complexometric titration.

The lignin obtained is then depolymerized under previously specified conditions.

The process of the invention thus makes it possible to obtain compounds containing a single aromatic ring having a weight-average molar mass of less than 2000 g/mol, preferably having a weight-average molar mass of less than 1500 g/mol in silylated form or having a weight-average molar mass of less than 450 g/mol, preferably having a weight-average molar mass of 400 g/mol (that is to say a degree of polymerization of 1 monomer unit), corresponding to formula (I). The nature of the aromatic compound obtained depends on the abundance of the G, H and S units in the lignin used. These G/H/S proportions depend on the plant species and also on the lignin extraction method. Consequently, the nature of the products obtained depends on the origin of the lignin and also on its extraction method. In the case of the use of a silane of formula (III) and of a catalyst, the lignin depolymerization makes it possible to obtain pure products, that is to say with a purity of greater than or equal to 90% by weight, preferably of between 90% and 99.9% by weight, relative to the total weight of the monocyclic aromatic compounds of formula (I), with good yields (from 10% to 70% by weight of monocyclic aromatic compound of formula (I) relative to the weight of starting lignin, for example), this being under mild reaction conditions.

As already indicated, in the process of the invention, the by-products possibly formed are generally oligomers bonded by non-cleavable bonds for the purposes of the invention and having physicochemical properties that are very different than those of the desired monocyclic aromatic compounds. This thus allows easy separation of the monocyclic aromatic compounds of formula (I) from the by-products, by conventional purification techniques (column chromatography or distillation, for example).

Thus, the process of the invention allows the lignin to become the main source of aromatic compounds of biological origin for the chemical industry. Aromatic compounds with high added values, for instance benzene, toluene, xylenes (BTX), substituted coniferols, phenol, aromatic polyols and quinines, can thus be obtained and used in the synthesis of phenol-formaldehyde resins, polyolefin-lignin polymers, polyester-lignin polymers, polyurethanes, bioplastics and epoxide resins.

The aromatic compounds obtained by means of the process of the invention can thus be used as starting materials in the construction sectors, and in the petrochemical, electrical, electronics, textile, aeronautical, pharmaceutical, cosmetics and agrochemical industry.

A subject of the invention is thus the use of the monocyclic aromatic compounds of formula (I) obtained by means of the process of the invention, in the production of fuels, electronic components, plastic polymers, rubber, medicaments, vitamins, cosmetic products, fragrances, foodstuffs, synthetic threads and fibers, synthetic leathers, adhesives, pesticides and fertilizers.

A subject of the invention is the use of the process for preparing monocyclic aromatic compounds of formula (I) according to the invention, in the production of fuels, electronic components, plastic polymers, rubber, medicaments, vitamins, cosmetic products, fragrances, foodstuffs, synthetic threads and fibers, synthetic leathers, adhesives, pesticides and fertilizers.

Another subject of the invention is a process for producing fuels, electronic components, plastic polymers, rubber, medicaments, vitamins, cosmetic products, fragrances, foodstuffs, synthetic threads and fibers, synthetic leathers, adhesives, pesticides and fertilizers, characterized in that it comprises a step of preparing monocyclic aromatic compounds of formula (I) by means of the process according to the invention.

Other advantages and characteristics of the present invention will emerge on reading the examples below, given by way of illustration and which are nonlimiting.

EXAMPLES

The synthesis of the chemical molecules of general formula (I), is carried out by following an approach which integrates three steps integrating the selection of the plant species, the extraction of the lignin and also a convergent reductive depolymerization method. The choice of the plant species from which the lignin will be extracted, the process for the extraction thereof and also the convergent depolymerization play an important role, in particular, with regard to the nature of the aromatic compound of formula (I) that it is sought to obtain and thus the selectivity of the process of the invention, with regard to the yield of the process of the invention, with regard to the degree of purity of said aromatic compound and with regard to the productivity. The lignin depolymerization step is carried out in the presence of a catalyst, by reacting a lignin having a sulfur content of less than 1.5% by weight relative to the total weight of the lignin, with a silane compound of formula (III) according to the following experimental protocol.

The reagents used, in particular the silane compound of formula (III) and the catalyst, are commercial products. General Experimental Protocol for the Synthesis of the Monocyclic Aromatic Compounds of Formula (I) from Lignin 1. Under an inert argon or nitrogen atmosphere, the silane compound of formula (III), the catalyst (from 1 to 0.001 molar equivalents calculated relative to the number of mole of lignin added) and half the amount of solvent are stirred in a glass container of suitable volume. The silane concentration in the reaction mixture varies from 1.0-6.0 mol·l$^{-1}$ (concentration calculated on the basis of half the final volume of solvent introduced).
2. Furthermore, in a Schlenk tube, the Organosolv lignin (10-40% of equivalent by weight of silane added), dried beforehand overnight by means of a vacuum gradient, is stirred with the remaining half of solvent.
3. The solution containing the catalyst and the silane compound of formula (III) is slowly added (addition times 15 minutes-1 hour) using a syringe and with stirring, to the Schlenk tube. The latter is left open in order to evacuate the gases produced by the reaction.
4. Once the addition of the solution is complete and the release of gas has stopped, the Schlenk tube is closed and left to stir. The starting lignin is then almost totally soluble. The reaction is monitored by GC-MS.
5. Once the reaction has ended (reaction time of 1 to 72 hours), the solvent and also the volatile compounds are evaporated off using a vacuum pump (10$^{-2}$ mbar). The viscous liquid obtained is purified by means of silica gel chromatography using an elution gradient of 100:0 to 0:100 of pentane: $CH_2Cl_2$ for the nonpolar fractions, and an elution gradient of 100:0 to 0:100 of $CH_2Cl_2$:EtOAc for the polar fractions. In the case where a fraction is very polar, the elution can be carried out with an EtOAc:MeOH mixture (50:50 to 0:100). It should be noted that, depending on the intended application, the purification step may optionally be omitted.
6. Finally, the various fractions resulting from the column are hydrolyzed in an acidic medium using 2 M HCL or $H_2SO_4$ in THF, or in a basic medium using 15% to 30% by weight of NaOH or KOH, or finally by means of a standard fluorinated reagent: HF-pyridine, TBAF, CsF or $NH_4F$ so as to provide the corresponding hydrolyzed product.

A set of results is presented below, giving examples of Organosolv lignin depolymerization.

The catalysts tested are $B(C_6F_5)_3$ and also the iridium complex ([(POCOP)Ir(H)(acetone)]$^+$B(C$_6$F$_5$)$_4^-$), the synthesis of which is described by I. Gottker-Schnetmann, P. White, and M. Brookhart, *J. Am. Chem. Soc.* 2004, 126, pages 1804-1811; and by J. Yang and M. Brookhart, *J. Am. Chem. Soc.* 2007, 129, pages 12656-12657.

The lignin used results from several processes of Organosolv type {a) Alcell: J. H. Lora, W. G. Glasser, *J Polym Environ*, 2002, 10, pages 39-48; b) Acetocell: Bojan Jankovic, *Bioresource Technol.*, 2011, 102, pages 9763-9771; c) Acetosolv: J. C. Parajo, J. L. Alonso, D. Vazquez, *Bioresource Technology*, 1993, 46, pages 233-240; d) ASAM: I. Miranda, H. Pereira, *Holzforschung*, 2002, 56, pages 85-90; e) Batelle/Genevaphenol: A. Johansson, O. Aaltonen, P. Ylinen, *Biomass* 1987, 13, pages 45-65; f) Formacell: X. F. Sun, R. C. Sun, P. Fowler, M. S. Baird, *Carbohydr. Polym.*, 2004, 55, pages 379-391; g) Milox: P. Ligero, A. Vega, J. J. Villaverde, *Bioresource Technol.*, 2010, 101, pages 3188-3193; h) Organocell: A. Lindner, G. Wegener, *J. Wood Chem. Technol.* 1988, 8, pages 323-340} and in particular the AVIDEL process (described by H. Q. Lam, Y. Le Bigot, M. Delmas, G. Avignon, *Industrial Crops and Products*, 2001, 14, pages 139-144) which constitutes an optimized version of the Formacell process.

The types of wood from which the lignins are derived are selected on the basis of the approach described in this invention in order to maximize the yield and also the selectivity toward a product.

The Synthesis of Trisubstituted Aromatic Molecules Using the Convergent Approach:

Using the data present in the literature as a basis, the species that can give compounds of formulae IIa and IIb with the best yields and selectivities are those containing:
 a G type lignin (according to the lignin classification);
 at least 10% by weight of lignin relative to the total weight of the sample of the selected plant species;
 at least 30% of cleavable bonds relative to the total number of bonds present between the monomer units in the lignin.

As it happens, the species which derive from the family Pinaceae, for instance pines, firs and cedars, meet these selection criteria. Likewise, a commercial mixture of several types of wood deriving from this family was used (F315), to show the versatility and also the robustness of the method.

Furthermore, the process used for extracting the lignin is chosen so as to modify the structure of the lignin of the selected species as little as possible. This makes it possible to keep the same types of functionalities and the same proportions of bonds present in the starting lignin, thereby contributing to increasing the overall yield and the selectivity toward a product. To do this, extraction methods of Organosols type were used in the context of this invention, and in particular the AVIDEL method, since they are known to give lignins of which the structure is very close to the initial lignin present in the species.

Moreover, the lignin depolymerization under reducing conditions according to the invention makes it possible to converge all the fragments obtained into a single final product. Thus, a silane of general formula (III) with a catalyst are used, in order to carry out the depolymerization reaction and also the reduction of the fragments obtained in order to converge toward a final product. The control of the selectivity toward the products IIa and IIb is carried out by varying the amount of silane and also the amount of the catalyst added.

Example 1: Synthesis of Compound IIa from the Lignin Derived from the Wood Mixture F315 (Extracted by Means of the AVIDEL Process) and with Triethylsilane (Et$_3$SiH)

The lignin derived from F315 sawdust (softwood) was extracted by means of the AVIDEL process (optimized in the literature for the extraction of lignin derived from straw), and was then depolymerized using the general procedure described above. The triethylsilane is used as a reducing agent with a weight ratio of triethylsilane to lignin of between 2.7 and 3.1. 20% by weight of catalyst (weight calculated relative to the weight of lignin added) are required to perform the conversion. The addition of the catalyst-silane mixture lasts between 30 and 45 minutes, the solution remains a dark brown color, and the reaction is left to stir for 24 h at 25° C. At the end of the reaction, followed by the evaporation of the solvent and of the volatile compounds, a gel having a weight of 60% of the weight of silane initially added is obtained. This product is purified using the same conditions as those described in the general procedure. At the end of this purification, compound IIa is obtained with a very high purity with a weight yield of from 10% to 20% relative to the weight of lignin used (nonoptimized). This product was characterized by GC-MS, $^{13}$C NMR, $^1$H NMR and HR-MS. Finally, the fractions resulting from the purification are hydrolyzed by stirring each fraction at 25° C. for 16 hours in the presence of a 2 M solution of HCl in THF. Finally, the polyols are obtained after evaporation of the solvent and of the volatile compounds.

Example 2: Synthesis of Compound IIb from the Lignin Derived from the Wood Mixture F315 (Extracted by Means of the AVIDEL Process) and with Triethylsilane (Et$_3$SiH)

The same procedure employed in example 1 is used. For obtaining compound IIb, however, the weight ratio of triethylsilane (Et$_3$SiH) to lignin introduced is 2.5. The weight yield obtained is between 27% and 32% relative to the weight of starting lignin introduced, with a very high purity (>99.7% by weight relative to the weight of the compounds of formula (II) obtained).

Example 3: Synthesis of Compound IIa from the Lignin Derived from Pine (*Pinus pinea*) (Extracted by Means of the AVIDEL Process) Using Triethylsilane (Et$_3$SiH)

The same procedure employed for the depolymerization of the wood mixture F315 is used for the depolymerization of the lignin derived from pine (softwood). Likewise, the products obtained in the two cases (pine and F315) are similar and compound IIa was obtained with a weight yield of 28% relative to the weight of starting lignin introduced, with a very high purity (>99.7% by weight relative to the weight of the compounds of formula (II) obtained).

Example 4: Synthesis of Compound IIa from the Lignin Derived from Norway Spruce (*Picea abies*) (Extracted by Means of the AVIDEL Process) Using Triethylsilane (Et$_3$SiH)

The same procedure employed for the depolymerization of the wood mixture F315 is used for the depolymerization of the lignin derived from Norway spruce (softwood). Likewise, the products obtained in the two cases (spruce and F315) are similar and the product IIa was obtained with a weight yield of 22% relative to the weight of starting lignin introduced.

Example 5: Depolymerization of the Lignin Derived from the F315[28] Sawdust Mixture (Extracted by Means of the AVIDEL Process) Using TMDS In the case where TMDS (tetramethyldisiloxane) is used as silane, gel formation is a possibility, which makes the reaction very difficult. To do this, two solutions can be envisioned: the dilution of the solution 3 to 4 times using CH$_2$Cl$_2$ as solvent or else the use of benzene or toluene as solvent. However, the reaction will be slower in the two cases envisioned. If the reaction is carried out in CH$_2$Cl$_2$, the TMDS concentration is about 1-3 mol·l$^{-1}$ (concentration calculated on the basis of half the final volume of solvent introduced). 20% by weight of B(C$_6$F$_5$)$_3$ (weight calculated relative to the weight of lignin added) are required to catalyze the reaction. The weight of lignin added is between 10% and 30% of the weight of the silane added. The addition time of the catalyst-silane mixture is spread out over between 30 and 45 minutes. The reaction is then left to stir for 24 hours at 25° C. At the end of the reaction, the volatile compounds and also the solvent are evaporated off under vacuum (10$^{-2}$ mbar). The mixture resulting from the depolymerization degrades during its purification on a silica column and the product II is hydrolyzed in a basic medium, using a mixture of THF and H$_2$O containing 10% by weight of NaOH. After stirring for 16 hours at 25° C., the volatile compounds and also the solvents are evaporated off, and the product is purified on a silica column.

Example 6: Depolymerization of the Lignin Derived from the Commercial Sawdust Mixture F315 (Extracted by Means of the AVIDEL Process) Using ([POCOP]Ir(H)(Acetone)]$^+$B(C$_6$F$_5$)$_4^-$) and Diethylsilane as Reducing Agent The depolymerization of the wood mixture F315 is carried out according to the general depolymerization procedure (described above). In the case where the ([POCOP]Ir (H)(acetone)]$^+$B(C$_6$F$_5$)$_4^-$) complex is used for the lignin depolymerization, the procedure is similar to that in which B(C$_6$F$_5$)$_3$ is used. Et$_2$SiH$_2$ (5 mol·l$^{-1}$) is used as reducing agent in chlorobenzene. The weight of lignin corresponds to 30% of the weight of the silane added. The reaction is carried out in the presence of 25% by weight of catalyst (weight calculated relative to the weight of lignin added). The addition time of the silane and of the catalyst is 30 minutes. The reaction time is about 24 hours. The solvent and the volatile compounds are then evaporated off, and the viscous liquid obtained is purified on a silica column (see general procedure). The products from the column are hydrolyzed by stirring the products for 16 h in a 2 M solution of HCl in THF. Finally, the various corresponding polyols are obtained by evaporation of the solvent and of the volatile compounds under vacuum.

The Synthesis of Tetrasubstituted Aromatic Molecules Using the Convergent Approach:

The species that can give molecules of formulae IIc and IId with the best yields and selectivities are those containing:
- a GS-type lignin (according to the lignin classification), with an S/G ratio greater than 1;
- at least 10% by weight of lignin relative to the total weight of the sample of the selected plant species;
- at least 30% of cleavable bonds relative to the total number of bonds present in the monomer units in the lignin.

As it happens, some species deriving from the angiosperm sub-branch, for example beech, birch, *eucalyptus* and oak, meet these selection criteria.

Furthermore, the process used for extracting the lignin is the same as that chosen for the synthesis of compounds IIa and IIb.

The lignin depolymerization step is the one used for the synthesis of compounds IIa and IIb. The selectivity toward the products IIc and IId is controlled by varying the amount of silane and also the amount of catalyst added. The best results were obtained with green oak (*Quercus ilex*).

Example 7: Synthesis of Compound IIc from the Lignin Derived from Green Oak (*Quercus ilex*) (Extracted by Means of the AVIDEL Process) Using Triethylsilane (Et₃SiH)

The depolymerization of green oak (hardwood) is carried out according to the general depolymerization procedure described above. The weight ratio of triethylsilane to lignin is between 2.7 and 3.1. The solvent used is CH₂Cl₂. The reaction is carried out in the presence of 30-40% by weight of catalyst (weight calculated relative to the weight of lignin added). The solution of silane and catalyst is added to the Schlenk tube over a period of 30 minutes and the reaction is left to stir for 24 hours at 25° C. At the end of the reaction and the evaporation of the solvent and of the volatile compounds, the viscous liquid obtained contains essentially compounds IIa and IIc with the relative proportions 82:18 IIc:IIa. The mixture is purified using the same conditions as described previously. The obtained weight yield of compound IIc is 35% relative to the weight of starting lignin introduced. Finally, the purified compounds IIa and IIc were hydrolyzed in an acidic medium using a 2 M solution of HCl in THF. After stirring for 16 hours at ambient temperature (20±5° C.), the solvent and also the volatile compounds are evaporated off, to provide the various corresponding polyols.

Example 8: Synthesis of Compound IId from the Lignin Derived from Green Oak (*Quercus ilex*) (Extracted by Means of the AVIDEL Process) Using Triethylsilane (Et₃SiH)

The same procedure employed in example 1 is used to obtain compound IIb, however the weight ratio of triethylsilane (Et₃SiH) to lignin introduced is from 2.5 to 2.7. The weight yield obtained is between 30% and 34% relative to the weight of starting lignin introduced, with a very high purity (>99.7%).

Example 9 (Comparative): Depolymerization with Triethylsilane (Et₃SiH) of the Commercial Lignin (Aldrich: Kraft Lignin) Derived from Softwood and then Desulfurized Using Sodium Hydroxide The same procedure employed for the depolymerization of the lignin derived from F315 sawdust (example 1) is used for the depolymerization of the lignin derived from the Kraft process and having a sulfur content of 3.76% by weight relative to the total weight of the lignin. No dissolution or depolymerization was observed in the case of this lignin. In the case where this same lignin sample is retreated by means of the AVIDEL process, given that this treatment makes it possible to decrease the degree of polymerization of the lignin and also to modify its structure, which allows easier depolymerization of the lignin. It should be noted that the sulfur content reaches 3% by weight relative to the total weight of the lignin. Despite the AVIDEL pretreatment, the depolymerization still does not take place. This implies that the presence of sulfur in the reaction medium plays a crucial role in the deactivation of the reaction.

The products of formulae IIa to IIf are identified and characterized by elemental analysis, by ¹H NMR and ¹³C NMR and by HR-MS (Shimadzu GCMS-QP2010 Ultra gas chromatograph mass spectrometer equipped with a Supelco SLB™-ms fused silica capillary column (30 m×0.25 mm×0.25 μm).

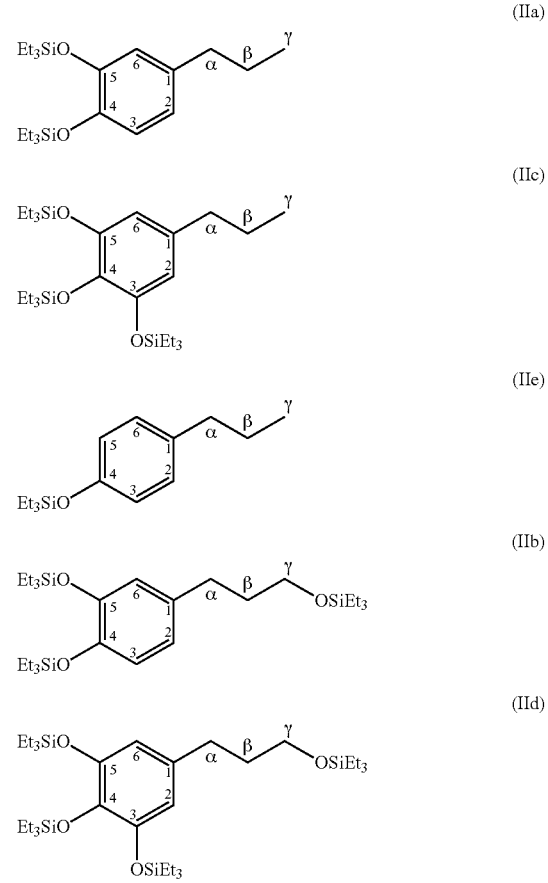

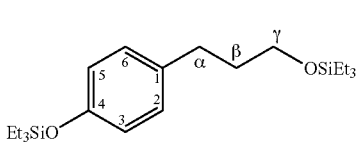
(IIf)

IIa:

¹H NMR (200 MHz, CDCl₃, Me₄Si) δ (ppm)=6.71 (1H, d, ³J=8.1 Hz, Ar—H), 6.63 (1H, s, Ar—H), 6.58 (1H, d, ³J=8.1 Hz, Ar—H), 2.45 (2H, t, ³J=7.8 Hz, Ar-CH₂), 1.57 (2 H, sex, ³J=7.8 Hz, CH₂—CH₃), 0.98 (18H, t, ³J=7.9 Hz, CH₃CH₂Si), 0.90 (3H, t, ³J=7.8 Hz, CH₃CH₂Si), 0.74 (12H, q, ³J=7.9 Hz, CH₃CH₂Si).

¹³C NMR (50 MHz, CDCl₃, Me₄Si): δ (ppm)=146.5, 144.7, 136.0, 121.3, 120.9, 120.2, 37.4, 24.7, 13.9, 6.9, 5.3, 5.2.

HR-MS (APPI): calculated (M+) (C₂₁H₄₀O₂Si₂), m/z 380.2566; found (M+), m/z 380.2559.

Anal. Calculated for C₂₁H₄₀O₂Si₂ (mol. wt. 380.72): C, 66.25; H, 10.59. Found: C, 66.18; H, 10.46.

MS: IE (m/z): 380 (9); 351 (4); 207 (8); 117 (4); 116 (11); 115 (100); 88 (7); 87 (74); 59 (45); 58 (4).

IIb:

¹H NMR (200 MHz, CDCl₃, Me₄Si) δ (ppm)=6.79-6.50 (3H, m, Ar—H), 3.60 (2H, t, ³J=6.6 Hz, CH₂—O), 2.54 (2H, t, ³J=7.6 Hz, Ar-CH₂), 1.79 (2H, quin, ³J=7.0 Hz, Ar—CH₂-CH₂), 1.05-0.88 (27H, m, CH₃CH₂Si), 0.84-0.48 (18H, m, CH₃CH₂Si).

¹³C NMR (50 MHz, CDCl₃, Me₄Si): δ (ppm)=146.5, 144.8, 135.4, 121.3, 120.9, 120.3, 62.3, 34.7, 31.5, 6.9, 6.8, 5.2, 5.2, 4.6.

MS: IE (m/z): 87 (100), 115 (57), 59 (38), 89 (28), 207 (24), 32 (16), 235 (11), 88 (10), 337 (9), 511 (8), 116 (6), 86 (6).

IIc:

¹H NMR (200 MHz, CDCl₃, Me₄Si) δ (ppm)=6.27 (2H, s, Ar—H), 2.39 (2H, t, ³J=7.5 Hz, Ar-CH₂), 1.69-1.45 (2H, m, CH₂—CH₃), 1.1-0.84 (27H, m, CH₃CH₂Si), 0.90-0.81 (3H, m, CH₃CH₂Si), 0.83-0.65 (18H, m, CH₃CH₂Si).

¹³C NMR (50 MHz, CDCl₃, Me₄Si): δ (ppm)=147.8, 146.5, 134.5, 113.6, 37.7, 24.6, 13.7, 7.0, 6.8, 5.4, 5.2.

MS: IE (m/z): 510 (8); 339 (4); 338 (10); 337 (31); 116 (7); 115 (60); 88 (10); 87 (100); 86 (4); 59 (49).

IId:

¹H NMR (200 MHz, CDCl₃, Me₄Si) δ (ppm)=6.28 (2H, s, Ar—H), 3.59 (2H, t, ³J=6.7 Hz, CH₂—O), 2.48 (2H, t, ³J=7.5 Hz, Ar-CH₂), 1.78 (2H, quin, ³J=7.3 Hz, Ar—CH₂—CH₂), 1.13-0.85 (36H, m, CH₃CH₂Si), 0.84-0.49 (24H, m, CH₃CH₂Si).

¹³C NMR (50 MHz, CDCl₃, Me₄Si): δ (ppm)=147.9, 136.6, 134.0, 113.6, 62.3, 34.6, 31.7, 6.9, 6.8, 5.4, 5.2, 4.5.

MS: IE (m/z): 87 (100), 115 (36), 59 (32), 89 (19), 641 (9), 88 (9), 467 (8), 365 (7), 337 (6), 642 (5), 640 (5), 116 (4).

IIe:

¹H NMR (200 MHz, CDCl₃, Me₄Si) δ (ppm)=7.03 (2H, d, ³J=7.7 Hz, Ar—H), 6.77 (2H, ³J=7.7 Hz, Ar—H), 2.52 (2H, t, ³J=7.3 Hz, Ar-CH₂), 1.61 (2H, sex, ³J=7.4 Hz, CH₂—CH₃), 1.09-0.86 (9H, m, CH₃CH₂Si), 0.97-0.85 (3H, m, CH₃CH₂Si), 0.83-0.64 (6H, m, CH₃CH₂Si).

¹³C NMR (50 MHz, CDCl₃, Me₄Si): δ (ppm)=153.5, 135.5, 129.4, 119.7, 37.4, 24.9, 13.9, 6.8, 5.1.

MS: IE (m/z): 250 (37), 222 (21), 221 (100), 193 (51), 165 (26), 163 (13), 151 (16), 135 (13), 91 (32), 87 (21), 82 (17), 59 (29), 43 (23).

IIf:

¹H NMR (200 MHz, CDCl₃, Me₄Si) δ (ppm)=7.03 (2H, d, ³J=8.7, Ar—H), 6.76 (2H, d, ³J=8.5, Ar—H), 3.61 (2H, t, ³J=6.8, CH₂—O), 2.60 (2H, t, J=7.8, Ar-CH₂); 1.87 (2H, quin, ³J=7.5, Ar—CH₂-CH₂); 1.08-0.89 (18H, m, CH₃CH₂Si), 0.81-0.50 (12H, m, CH₃CH₂Si).

¹³C NMR (50 MHz, CDCl₃, Me₄Si): δ (ppm)=153.6, 134.9, 129.4, 119.8, 62.3, 34.7; 31.4, 7.0, 6.8, 5.1, 4.6.

MS: IE (m/z): 380 (6), 352 (11), 351 (26), 248 (53), 219 (57), 161 (18), 147 (21), 133 (21), 119 (10), 91 (18), 89 (100), 87 (55), 75 (16), 59 (45).

Experimental Protocol for Hydrolysis of Silylated Aromatic Compounds Resulting from the Reductive Depolymerization of Lignin A nBu₄NF.3H₂O (315.5 mg, 2.1 mmol, 2.1 equiv) was slowly added (approximately 5 min), under argon, to a solution of IIa (380.7 mg; 1.0 mmol, 1 equivalent) in 4 ml of THF. The solution was stirred for 1 h at 20° C. The volatile compounds were then evaporated off under vacuum and 4 ml of dichloromethane were added. Finally, compound IIa was purified on a silica column using an elution gradient ranging from 50% dichloromethane to 50% ethyl acetate. The evaporation of the solvents results in the obtaining of 4-propylbenzene-1,2-diol (141.5 mg; 0.9 mmol; 84%) in the form of a colorless oil.

Table 1 reproduces the results of the hydrolysis of the silylated aromatic molecules IIa-IIf resulting from the reductive depolymerization of the lignins of the examples indicated above.

TABLE 1

| Silylated aromatic molecule | Amount of TBAF (equiv.) | Appearance | Isolated yield (%) |
| --- | --- | --- | --- |
| IIa | 2.1 | colorless oil | 84 |
| IIb | 3.1 | colorless oil | 86 |
| IIc | 3.1 | white powder or colorless crystals | 94 |
| IId | 4.1 | white gum | 82 |
| IIe | 1.1 | colorless oil | 77 |
| IIf | 2.1 | white powder | 92 |

After the hydrolysis, all the O—Si bonds are converted to O—H.

The invention claimed is:

1. A process for preparing monocyclic aromatic compounds of formula (I)

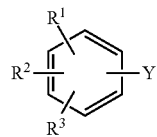

(I)

in which
R¹, R² and R³ represent, independently of one another, a hydrogen atom, a hydroxyl group, an alkoxy group or a siloxy group;
Y represents an alkyl group, an alkenyl group, an alkynyl group, or a carbonyl group —CR⁴=O with R⁴ representing a hydrogen atom, an alkyl group, a hydroxyl group or an alkoxy group, said alkyl, alkenyl and alkynyl groups being optionally substituted;

characterized in that it comprises a step of depolymerization of the lignin by selective cleavage of the carbon sp$^3$-oxygen bond of the alkylaryl ethers of the β-O-4, α-O-4, β-5, β-1 and β-β type present in the lignin, said depolymerization step comprising the reaction, of a lignin containing a sulfur content of less than 1.5% by weight, relative to the total weight of the lignin, with a silane compound of formula (II)

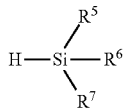

(III)

in which
R$^5$, R$^6$ and R$^7$ represent, independently of one another, a hydrogen atom, a halogen atom, a hydroxyl group, an alkyl group, an alkenyl group, an alkynyl group, an alkoxy group, an aryloxy group, a silylated group, a siloxy group, an aryl group or an amino group, said alkyl, alkenyl, alkynyl, alkoxy, silylated, siloxy, aryl and amino groups being optionally substituted, or R$^7$ is as defined above and R$^5$ and R$^6$, taken together with the silicon atom to which they are bonded, form an optionally substituted, silylated heterocycle;

in the presence of a catalyst chosen from:
an organic catalyst chosen from:
carbocations chosen from the trityl cation ($(C_6H_5)_3C^+$), tropilium $(C_7H_7)^+$, the benzyl cation ($C_6H_5CH_2^+$), the allyl cation ($CH_3$—$CH^+$—$CH$=$CH_2$), methylium ($CH_3^+$), cyclopropylium ($C_3H_5^+$), the cyclopropyl carbocation chosen from the dimethylcyclopropyl carbocation and the dicyclopropyl carbocation, the triazabicyclodecene (TBD) cation, acylium ($R^1$—C≡O)$^+$ with R$^1$ chosen from methyl, propyl and benzyl, benzenium $(C_6H_5)^+$, and the norbornyl cation $(C_7H_{11})^+$;
oxoniums chosen from $(CH_3)_3O^+BF_4^-$ and $(CH_3CH_2)_3O^+BF_4^-$;
a silylium ion chosen from Et$_3$Si$^+$ and Me$_3$Si$^+$;
disilyl cations having a bridging hydride, chosen from the formula indicated below

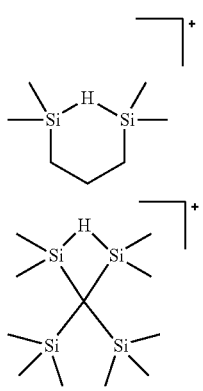

with the counterion of said silylium ion, said carbocations and of said disilyl cations being
a halide chosen from F$^-$, Cl$^-$, Br$^-$ and I$^-$; or
an anion chosen from BF$_4^-$, SbF$_6^-$, B(C$_6$F$_5$)$_4^-$, B(C$_6$H$_5$)$_4^-$, CF$_3$SO$_3^-$ and PF$_6^-$;

an organometallic catalyst chosen from:
the iridium complexes of formula (IV),

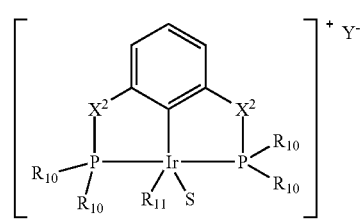

(IV)

in which
R$^{10}$ represents an alkyl or aryl group;
R$^{11}$ represents a hydrogen atom or an alkyl group;
X$^2$ represents a —CH$_2$— group or an oxygen atom;
Y$^-$ represents a counterion chosen from B(C$_6$F$_5$)$_4^-$ and B(C$_6$H$_5$)$_4^-$; and
S represents a solvent molecule, coordinated to the complex, chosen from dimethyl sulfoxide (DMSO), acetonitrile (CH$_3$CN) and acetone (CH$_3$COCH$_3$); and the ruthenium complexes of formula (V)

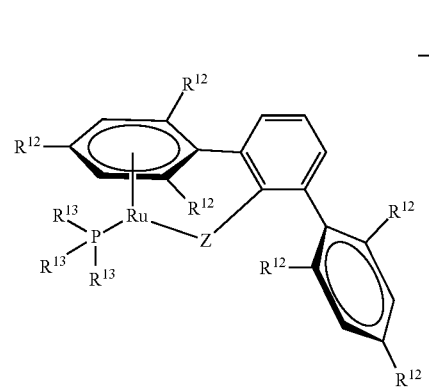

(V)

in which
R$^{12}$ represents a hydrogen atom or an alkyl group;
R$^{13}$ represents an aryl or an alkyl group, said aryl and alkyl groups being optionally substituted;
Z represents a —CH$_2$— group, an oxygen atom or a sulfur atom; and
A$^-$ represents a counterion chosen from B(C$_6$F$_5$)$_4^-$ and [CHB$_{11}$H$_5$Cl$_6$]$^-$;

an organometallic and metallic catalyst chosen from:
boron compounds chosen from BF$_3$, BF$_3$(Et$_2$O), BCl$_3$, BBr$_3$, triphenyl hydroborane, tricyclohexyl hydroborane, B(C$_6$F$_5$)$_3$, B-methoxy-9-borabicyclo[3.3.1]nonane (B-methoxy-9-BBN) and B-benzyl-9-borabicyclo[3.3.1]nonane (B-benzyl-9-BBN);
the borenium compound Me-TBD-BBN$^+$, borenium ferrocene derivatives corresponding to the formula

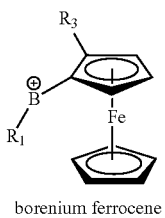

borenium ferrocene in which R¹=phenyl and R³=3,5-dimethylpyridyl;
aluminum compounds chosen from AlCl₃, AlBr₃, aluminum isopropoxide Al(O-i-Pr)₃, aluminum ethanoate (Al(C₂H₃O₂)), the Krossing salt [Ag(CH₂Cl₂)]{Al[OC(CF₃)₃]₄}, Li{Al[OC(CF₃)₃]₄} and Et₂Al⁺;
indium compounds chosen from InCl₃ and In(OTf)₃;
iron compounds chosen from FeCl₃ and Fe(OTf)₃;
tin compounds chosen from SnCl₄ and Sn(OTf)₂;
phosphorus compounds chosen from PCl₃, PCl₅ and POCl₃;
trifluoromethanesulfonate or triflate compounds (CF₃SO₃⁻) of transition metals and lanthanides chosen from scandium triflate, ytterbium triflate, yttrium triflate, cerium triflate, samarium triflate and niodinium triflate.

2. The process as claimed in claim 1, wherein, in the monocyclic aromatic compound of formula (I)
R¹, R² and R³ represent, independently of one another, a hydrogen atom; a hydroxyl group; an alkoxy group of which the alkyl group is chosen from methyl, ethyl, propyl and butyl groups and branched isomers thereof; a siloxy (—O—Si(X)₃) group in which each X, independently of one another, is chosen from a hydrogen atom, an alkyl group chosen from methyl, ethyl and propyl groups, an aryl group chosen from phenyl and benzyl, a polymeric organosilane of general formula

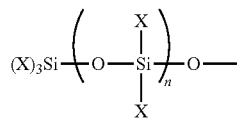

in which X is as defined above and n is an integer between 1 and 20 000, advantageously between 1 and 5000, more advantageously between 1 and 1000;
Y represents an alkyl group chosen from methyl, ethyl, propyl and butyl groups and branched isomers thereof; a carbonyl —CR⁴=O group with R⁴ representing a hydrogen atom; an alkyl group chosen from methyl, ethyl, propyl and butyl groups and branched isomers thereof; and a hydroxyl group;
said alkyl groups being optionally substituted with one or more hydroxyl groups; one or more siloxy (—O—Si(X)₃) groups in which each X, independently of one another, is chosen from a hydrogen atom, an alkyl group chosen from methyl, ethyl and propyl groups, an aryl group chosen from phenyl and benzyl, a polymeric organosilane of general formula

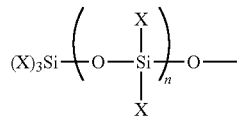

in which X is as defined above and n is an integer between 1 and 20 000.

3. The process as claimed in claim 1, wherein the monocyclic aromatic compound of formula (I)
R¹, R² and R³ represent, independently of one another, a hydrogen atom; a hydroxyl group; an alkoxy group of which the alkyl group is a methyl group or an ethyl group;
a siloxy (—O—Si(X)₃) group in which each X, independently of one another, is a hydrogen atom, a methyl group, an ethyl group, a phenyl group, polydimethylsiloxane (PDMS), polymethylhydroxysiloxane (PMHS) or tetramethyldisiloxane (TMDS);
Y represents an alkyl group chosen from methyl, ethyl, propyl and butyl groups and branched isomers thereof; a carbonyl —CR⁴=O group with R⁴ representing a hydrogen atom; an alkyl group chosen from methyl, ethyl, propyl and butyl groups and branched isomers thereof; and a hydroxyl group;
said alkyl groups being optionally substituted with one or more hydroxyl groups; one or more siloxy (—O—Si(X)₃) groups in which each X, independently of one another, is chosen from a hydrogen atom, a methyl group, an ethyl group, a phenyl group, polydimethylsiloxane (PDMS), polymethylhydroxysiloxane (PMHS) and tetramethyldisiloxane (TMDS).

4. The process as claimed in claim 1, wherein the silane compound of formula (III), R⁵, R⁶ and R⁷ represent, independently of one another, a hydrogen atom; an alkyl group chosen from methyl, ethyl, propyl and butyl groups and branched isomers thereof; a siloxy (—O—Si(X)₃) group in which each X, independently of one another, is an alkyl group chosen from methyl, ethyl, propyl and butyl groups and branched isomers thereof; an alkoxy group of which the alkyl group is chosen from methyl, ethyl, propyl and butyl groups and branched isomers thereof; an aryl group chosen from phenyl and benzyl groups; said alkyl and aryl groups being optionally substituted.

5. The process as claimed in claim 1, wherein the silane compound of formula (III), R⁵, R⁶ and R⁷ represent, independently of one another, a hydrogen atom; an alkyl group chosen from methyl, ethyl and propyl groups; or an aryl group chosen from benzyl and phenyl groups.

6. The process as claimed in claim 1, wherein the lignin depolymerization uses a lignin containing at least 30% of cleavable bonds relative to the total number of bonds present between the monomer units in the lignin.

7. The process as claimed in claim 1, wherein the lignin depolymerization uses a lignin containing at least 30% of bonds of the β-O-4 type and/or at least 3% of α-O-4 bonds, the percentages indicated corresponding to the percentage of a type of bond relative to the total number of bonds present between the monomer units in the lignin.

8. The process as claimed in claim 1, wherein the lignin depolymerization uses a lignin of which the sulfur content is greater than or equal to zero and remains less than 1.5% by weight, relative to the total weight of the lignin, as defined below:

0≤sulfur content of the lignin<1.5% by weight, relative to the total weight of the lignin.

9. The process as claimed in claim 1, wherein the organometallic catalyst is chosen from:
the iridium complex [(POCOP)Ir(H)(acetone)]⁺B(C₆F₅)₄⁻ with (POCOP) representing 2,6-bis(di-tert-butylphosphinito)phenyl; and the ruthenium complex of formula (V) in which
$R^{12}$ represents a methyl group;
$R^{13}$ represents p-$FC_6H_4$;
Z represents a sulfur atom; and
$A^-$ represents $B(C_6F_5)_4^-$.

10. The process as claimed in claim 1, wherein the catalyst is chosen from $BF_3$; $InCl_3$; and triphenylcarbenium tetrakis(perfluorophenyl)borate [$(Ph)_3C^+B(C_6F_5)_4$, $B(C_6F_5)_3$].

11. The process as claimed in claim 1, wherein the depolymerization step, the reaction is carried out under a pressure of a or a mixture of inert gas(es) chosen from nitrogen and argon, or gases generated by the process, in particular methane and hydrogen.

12. The process as claimed in claim 11, wherein the pressure is between 0.2 and 50 bar, limits included.

13. The process as claimed in claim 1, wherein the depolymerization step, the reaction is carried out at a temperature of between 0 and 150° C., limits included.

14. The process as claimed in claim 1, wherein the depolymerization step, the reaction is carried out in a or a mixture of at least two solvent(s) chosen from:
  silylated ethers chosen from 1,1,1,3,3,3-hexamethyldisiloxane (($Me_3Si)_2O$) and 1,1,1,3,3,3-hexaethyldisiloxane (($Et_3Si)_2O$);
  hydrocarbons chosen from benzene, toluene, pentane and hexane;
  sulfoxides chosen from dimethyl sulfoxide (DMSO);
  alkyl halides chosen from chloroform, methylene chloride, chlorobenzene and dichlorobenzene.

15. The process as claimed in claim 1, wherein in the depolymerization step, the weight ratio between the silane compound of formula (III) and the lignin is between 0.5 and 6, limits included.

16. The process as claimed in claim 1, wherein the amount of catalyst is from 0.001 to 1 weight equivalent, limits included, relative to the initial weight of the lignin.

17. The process as claimed in claim 1 wherein, prior to the lignin depolymerization step, the plant species from which the lignin originates is selected so as to have:
  at least 10% by weight of lignin relative to the total weight of the sample of the plant species selected;
  at least 30% of cleavable bonds relative to the total number of bonds present between the monomer units in the lignin; and
  at least 50% of G, H or S residue relative to the total number of residues present in the lignin used.

18. The process as claimed in claim 17, wherein the plant species is chosen from
  cedars, pines, spruces and firs for targeting the formation of a monocyclic aromatic compound of formula (I) having a structure derived from the G unit; or
  poplars, oaks and eucalyptuses for the purpose of generating a monocyclic aromatic compound of formula (I) having a structure derived from the S unit.

* * * * *

UNITED STATES PATENT AND TRADEMARK OFFICE
CERTIFICATE OF CORRECTION

PATENT NO. : 10,081,644 B2
APPLICATION NO. : 15/323547
DATED : September 25, 2018
INVENTOR(S) : Feghali et al.

Page 1 of 1

It is certified that error appears in the above-identified patent and that said Letters Patent is hereby corrected as shown below:

In the Claims

Column 32,
Line 3, "F⁻, Cl⁻, Bf⁻ and I⁻" should read --F⁻, Cl⁻, Br⁻ and I⁻--.

Signed and Sealed this
Twenty-sixth Day of February, 2019

Andrei Iancu
*Director of the United States Patent and Trademark Office*